United States Patent
Jung et al.

(10) Patent No.: US 10,995,378 B2
(45) Date of Patent: May 4, 2021

(54) L-TRYPTOPHAN EXPORTER AND METHOD OF PRODUCING L-TRYPTOPHAN USING THE SAME

(71) Applicant: CJ Cheiljedang Corporation, Seoul (KR)

(72) Inventors: Moo Young Jung, Gyeonggi-do (KR); Chang Il Seo, Incheon (KR); Hyo Jin Kim, Gyeonggi-do (KR); Tae Yeon Kim, Gyeonggi-do (KR); Hyun Ah Kim, Gyeonggi-do (KR); Sung Kwang Son, Gyeonggi-do (KR); Hye Ryun Yoo, Gyeonggi-do (KR); Jae Min Lee, Gyeonggi-do (KR); Ki Yong Cheong, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/479,749

(22) PCT Filed: Feb. 22, 2019

(86) PCT No.: PCT/KR2019/002238
§ 371 (c)(1),
(2) Date: Jul. 22, 2019

(87) PCT Pub. No.: WO2019/164348
PCT Pub. Date: Aug. 29, 2019

(65) Prior Publication Data
US 2020/0063219 A1    Feb. 27, 2020

(30) Foreign Application Priority Data
Feb. 23, 2018    (KR) .................. 10-2018-0022054

(51) Int. Cl.
| C12P 13/22 | (2006.01) |
| C12N 1/21 | (2006.01) |
| C07K 14/195 | (2006.01) |
| C12R 1/19 | (2006.01) |
| C12N 15/70 | (2006.01) |
| C12N 15/77 | (2006.01) |
| C12R 1/15 | (2006.01) |

(52) U.S. Cl.
CPC .............. *C12R 1/19* (2013.01); *C12N 15/70* (2013.01); *C12N 15/77* (2013.01); *C12P 13/227* (2013.01); *C12R 1/15* (2013.01)

(58) Field of Classification Search
None
See application file for complete search history.

(56) References Cited

FOREIGN PATENT DOCUMENTS

| EP | 1016710 A2 | 7/2000 |
| EP | 1016710 B1 | 3/2010 |
| KR | 10-2003-0002295 A | 1/2003 |
| KR | 10-2005-0044860 A | 5/2005 |
| KR | 10-0791794 B1 | 1/2008 |
| WO | 97/23597 A2 | 7/1997 |

OTHER PUBLICATIONS

Jung et al., "*Herbaspirillum rhizosphaerae* sp. nov., isolated from rhizosphere soil of *Allium victorialis* var. *platyphyllum*", Int. J. Syst. Evol. Microbiol. 57:2284-2288, 2007 (Year: 2007).*
Palego et al., "Tryptophan Biochemistry: Structural, Nutritional, Metabolic, and Medical Aspects in Humans", J. Amino Acids 2016:8952520, 13 pages (Year: 2016).*
Oliveira et al., Front. Microbiol. 8:1937, 2017, 18 pages (Year: 2017).*
Pascual et al., Int. J. Sys. Bacteriol. 45:724-728, 1995 (Year: 1995).*
Author unknown, Drug/metabolite DMT transporter permease [Herbaspirillum rhizosphaerae], NCBI, GenBank accession No. WP_050478745.1, Oct. 16, 2017, 1 page.
Doroshenko et al., "YddG from *Escherichia coli* promotes export of aromatic amino acids", FEMS Microbiol Lett., 2007, vol. 275, pp. 312-318.
Zhang et al., "Rational engineering of multiple module pathways for the production of l-phenylalanine in Corynebacterium glutamicum", J Ind Microbial Biotechnol, 2015, vol. 42, pp. 787-797.

* cited by examiner

*Primary Examiner* — David Steadman
(74) *Attorney, Agent, or Firm* — MH2 Technology Law Group, LLP

(57) ABSTRACT

The present disclosure relates to a microorganism producing L-tryptophan in which the microorganism is modified such that a protein having an L-tryptophan-exporting activity comprising the amino acid sequence of SEQ ID NO: 1 is expressed, and a method for producing L-tryptophan using the microorganism.

4 Claims, 1 Drawing Sheet
Specification includes a Sequence Listing.

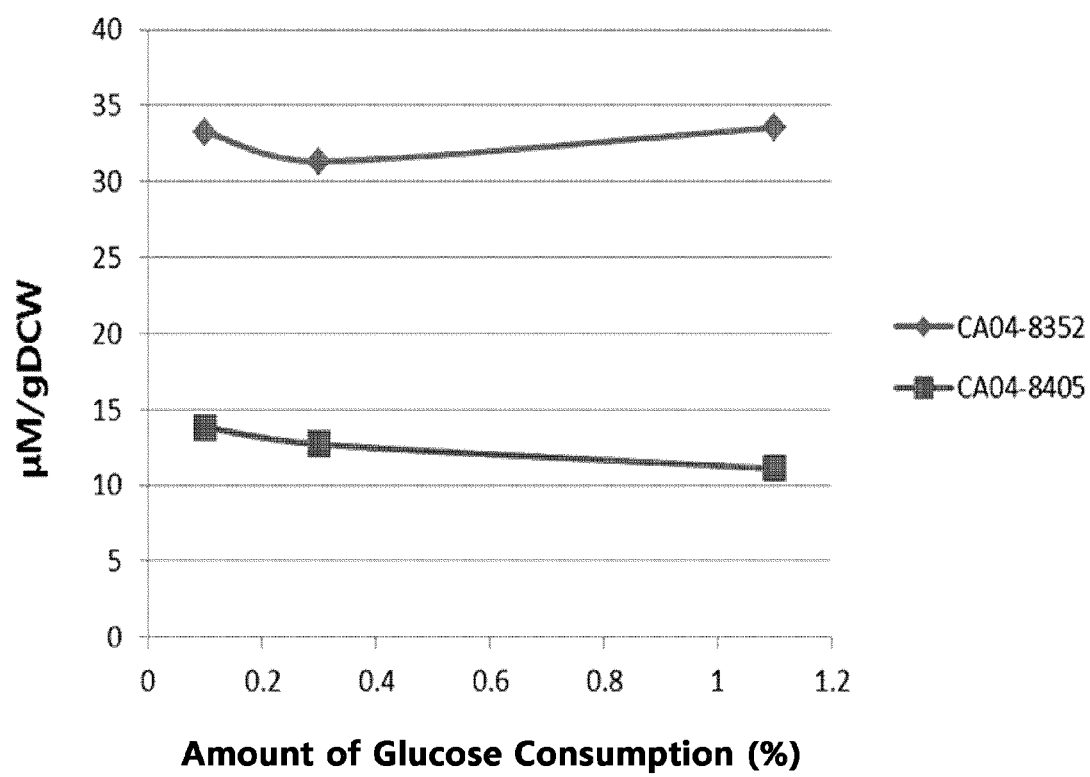

SEQUENCE LISTING

```
<160> NUMBER OF SEQ ID NOS: 77

<210> SEQ ID NO 1
<211> LENGTH: 307
<212> TYPE: PRT
<213> ORGANISM: Artificial Sequence
<220> FEATURE:
<223> OTHER INFORMATION: wex AA seq.

<400> SEQUENCE: 1

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
                20                  25                  30

Ala Thr Gly Gly Ala Ala Met Met Tyr Ser Val Ala Ser Leu Phe Leu
            35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305
```

```
<210> SEQ ID NO 2
<211> LENGTH: 924
<212> TYPE: DNA
<213> ORGANISM: Artificial Sequence
<220> FEATURE:
<223> OTHER INFORMATION: wex NT seq.

<400> SEQUENCE: 2
atgaatagca agaaggccac gctgatcgga cttactgcag tggtcctctg gagttccatt     60
gtcggattga ttcgcggcgt cagcgaacat ctcggcgcta ccgggggcgc ggcgatgatg    120
tatagcgttg cctcgctgtt tctgctgttg tcggtcggtt tcccgaaact gggttccttt    180
ccgaaaaaat acctcttgtg gggcagcctg ctgtttgtgt cctacgaact ctgcctgtcg    240
ctctccatcg gttatgccaa tacaggcagg caagcaatcg aagtcagcat ggtcaactat    300
ctgtggccgg cattcacgct catcgccgcc attgcattca accggcagag agcgaactgg    360
atggtggtgc ccggattcat cctctcgatt atcggtatct gctgggtgct gggcggtgac    420
caggggctgg acctggcggg catgcttggc aacgtgcagg acaatccgct cagttatggg    480
ctggcttttt tgggcgccgt gatctgggcc gcctattgca ctgtgacggc ccgcctcgcg    540
aaggggaaga acggagtgac gctgttcttc attcttgtgg cattgacgct ctgggtgaag    600
ttttcttcg gcgatcaccg cccgatgtct ttcagcctgc cggcaattgt ctacctgctc    660
ctggcggcgg ccgcgatggg cttcggctat gcggcatgga atgtcgggat cttgcacggt    720
aacgtgaccg tgctggcggg cgtgtcgtac tttatcccgg tttttcggc ggcgttgtcc    780
gcgatggtgt tgcatgcgcc gttgccgcga tcgttttggg tggggcgtc gctggtatgc    840
gccggttcga tactgtgctg gctggcaacc agggccaggc gcgcttcggc cgcgcaagaa    900
gatgcggtgg cggactgttt gtag                                           924

<210> SEQ ID NO 3
<211> LENGTH: 35
<212> TYPE: DNA
<213> ORGANISM: Artificial Sequence
<220> FEATURE:
<223> OTHER INFORMATION: wex - 1

<400> SEQUENCE: 3
tagaggagac acaacatgaa tagcaagaag gccac                                35

<210> SEQ ID NO 4
<211> LENGTH: 35
<212> TYPE: DNA
<213> ORGANISM: Artificial Sequence
<220> FEATURE:
<223> OTHER INFORMATION: wex - 2

<400> SEQUENCE: 4
ggctcttcct gtttagtcta caaacagtcc gccac                                35

<210> SEQ ID NO 5
<211> LENGTH: 35
<212> TYPE: DNA
<213> ORGANISM: Artificial Sequence
<220> FEATURE:
<223> OTHER INFORMATION: PgapA(-wex) - 1

<400> SEQUENCE: 5
cccttccggt ttagtttgaa gccagtgtga gttgc                                35
```

```
<210> SEQ ID NO 6
<211> LENGTH: 39
<212> TYPE: DNA
<213> ORGANISM: Artificial Sequence
<220> FEATURE:
<223> OTHER INFORMATION: PgapA(-wex) - 2

<400> SEQUENCE: 6
cttcttgcta ttcatgttgt gtctcctcta aagattgta                           39

<210> SEQ ID NO 7
<211> LENGTH: 20
<212> TYPE: DNA
<213> ORGANISM: Artificial Sequence
<220> FEATURE:
<223> OTHER INFORMATION: Confirm_PgapA-wex - 1

<400> SEQUENCE: 7
cggattatgc caatgatgtg                                                20

<210> SEQ ID NO 8
<211> LENGTH: 20
<212> TYPE: DNA
<213> ORGANISM: Artificial Sequence
<220> FEATURE:
<223> OTHER INFORMATION: Confirm_PgapA-wex - 2

<400> SEQUENCE: 8
cacgatcacc aacattcagg                                                20

<210> SEQ ID NO 9
<211> LENGTH: 314
<212> TYPE: PRT
<213> ORGANISM: Artificial Sequence
<220> FEATURE:
<223> OTHER INFORMATION: Pst AA seq.

<400> SEQUENCE: 9
```

Met Lys Asn Gln Arg Lys Ala Thr Leu Ile Gly Leu Val Ala Ile Val
1               5                   10                  15

Leu Trp Ser Ser Ile Val Gly Leu Ile Arg Gly Val Ser Glu Ser Leu
            20                  25                  30

Gly Ala Thr Gly Gly Ala Val Met Met Tyr Ser Val Ala Ser Val Met
        35                  40                  45

Leu Leu Phe Thr Val Gly Phe Pro Arg Ile Arg Glu Phe Pro Arg Arg
    50                  55                  60

Tyr Leu Val Trp Gly Ser Leu Leu Phe Val Ser Tyr Glu Leu Cys Leu
65                  70                  75                  80

Ala Leu Ser Ile Gly Tyr Ala Asn Ser Ser Arg Gln Ala Ile Glu Val
                85                  90                  95

Gly Met Val Asn Tyr Leu Trp Pro Ala Phe Thr Ile Leu Ala Ala Ile
            100                 105                 110

Leu Phe Asn Arg Gln Gln Ala Asn Leu Leu Ile Val Pro Gly Phe Leu
        115                 120                 125

Ile Ala Ile Leu Gly Ile Cys Trp Val Leu Gly Gly Glu Gln Gly Leu
    130                 135                 140

Asp Leu Ser Gly Met Thr Ala Asn Ile Arg Asp Asn Pro Leu Ser Tyr
145                 150                 155                 160

Gly Leu Ala Phe Ala Gly Ala Val Ile Trp Ala Ala Tyr Cys Thr Val
                165                 170                 175

```
Thr Thr Arg Ile Ala Gly Gly Lys Asn Gly Val Thr Leu Phe Phe Met
            180                 185                 190

Leu Thr Ala Leu Ala Leu Trp Ala Lys Tyr Leu Ala Ile Gly Gly Glu
        195                 200                 205

Thr Met Glu Phe Ser Tyr His Ala Leu Ile Tyr Leu Val Leu Ala Ala
    210                 215                 220

Ser Ala Met Gly Phe Gly Tyr Ala Ala Trp Asn Val Gly Ile Leu His
225                 230                 235                 240

Gly Asn Val Thr Val Leu Ala Gly Ala Ser Tyr Phe Ile Pro Val Leu
                245                 250                 255

Ser Ala Ala Leu Ala Ala Val Leu Leu Arg Thr Pro Leu Ser Leu Ser
            260                 265                 270

Phe Trp Gln Gly Ala Ala Met Val Cys Ile Gly Ser Ile Leu Cys Trp
        275                 280                 285

Phe Ala Thr Arg Ala Lys Pro Pro Glu Ser Ala Gln Ser Gly Asp Gln
    290                 295                 300

Ala Ser Ala Thr Thr Pro Arg Arg Asn Gly
305                 310
```

<210> SEQ ID NO 10
<211> LENGTH: 945
<212> TYPE: DNA
<213> ORGANISM: Artificial Sequence
<220> FEATURE:
<223> OTHER INFORMATION: Pst NT seq.

<400> SEQUENCE: 10

```
atgaaaaacc agcgtaaagc gaccctcatc gggctcgttg caattgtctt gtggagctcg      60
atcgtcggcc tgatccgggg cgtcagcgag agcctcggcg cgaccggtgg tgccgtcatg     120
atgtacagcg tcgcatcggt aatgctgttg ttcacggtcg gctttccgcg gatacgggag     180
ttcccccgac gctatcttgt ctggggcagc ctgctgttcg tctcgtacga gctgtgcctt     240
gccctgtcca tcggctacgc caacagcagc cgacaggcca tcgaggtcgg catggtcaat     300
tacctgtggc cggccttcac gatcctggcg gcgatcctgt tcaacaggca gcaggccaac     360
ctgctcatcg ttcccggctt cctcatcgcg atcctcggga tctgctgggt gctcggcggg     420
gaacaggggc tggacctgtc cgggatgacg gcgaacatcc gcgacaatcc cctcagctac     480
gggctggcct tcgccggcgc ggtgatctgg gcggcatact gcacggtgac cacgcggatc     540
gccggcggca agaacggtgt cacgctgttc ttcatgctga cggcattggc gctatgggcc     600
aagtacctgg ccatcggcgg ggaaacgatg gaattcagct accacgcgct gatctacctg     660
gtgctggccg cctccgcgat gggcttcggc tatgcggcgt ggaacgtcgg catcctgcac     720
ggcaatgtca ccgtcctcgc tggtgcttcg tatttcatcc cggtgctgtc cgccgccctg     780
gcggccgtac tgttgcgtac gccgctgtcg ctgtcgttct ggcagggtgc cgccatggtc     840
tgcatcgggt cgatcctctg ctggttcgcc acccgtgcga aaccgccaga atcggcgcag     900
tcgggtgacc aggccagcgc aaccacgccg cgtcgaaacg gataa                    945
```

<210> SEQ ID NO 11
<211> LENGTH: 35
<212> TYPE: DNA
<213> ORGANISM: Artificial Sequence
<220> FEATURE:
<223> OTHER INFORMATION: Pst-1

<400> SEQUENCE: 11
tagaggagac acaacatgaa aaccagcgt aaagc          35

<210> SEQ ID NO 12
<211> LENGTH: 35
<212> TYPE: DNA
<213> ORGANISM: Artificial Sequence
<220> FEATURE:
<223> OTHER INFORMATION: Pst-2

<400> SEQUENCE: 12
ggctcttcct gtttagttta tccgtttcga cgcgg          35

<210> SEQ ID NO 13
<211> LENGTH: 39
<212> TYPE: DNA
<213> ORGANISM: Artificial Sequence
<220> FEATURE:
<223> OTHER INFORMATION: PgapA(-Pst)-2

<400> SEQUENCE: 13
acgctggttt ttcatgttgt gtctcctcta aagattgta          39

<210> SEQ ID NO 14
<211> LENGTH: 303
<212> TYPE: PRT
<213> ORGANISM: Artificial Sequence
<220> FEATURE:
<223> OTHER INFORMATION: Afa AA seq.

<400> SEQUENCE: 14

```
Met Lys Gln Ser Asp Lys Ala Thr Leu Ile Gly Leu Ile Ala Ile Val
1               5                   10                  15

Leu Trp Ser Thr Ile Val Gly Leu Ile Arg Ser Val Ser Asp Ser Leu
            20                  25                  30

Gly Val Thr Gly Gly Ala Ala Leu Ile Tyr Thr Leu Ala Ser Val Phe
        35                  40                  45

Leu Leu Leu Ser Val Gly Trp Val Arg Leu Arg Asp Phe Pro Arg Arg
    50                  55                  60

Tyr Leu Ile Trp Gly Ser Val Leu Phe Val Cys Tyr Glu Leu Cys Leu
65                  70                  75                  80

Ala Leu Ser Ile Gly Tyr Ala His Asn Ser Gln Gln Ala Ile Glu Val
                85                  90                  95

Gly Met Val Asn Tyr Leu Trp Pro Thr Phe Thr Ile Val Ala Ala Ile
            100                 105                 110

Leu Phe Asn Lys Gln Lys Ala Asn Gly Leu Leu Ala Pro Gly Leu Leu
        115                 120                 125

Leu Ser Met Met Gly Ile Ser Trp Ile Leu Gly Gly Glu Gln Gly Leu
    130                 135                 140

Ser Leu His Asn Ile Trp Leu Asn Val Gln Asp Asn Pro Leu Ser Tyr
145                 150                 155                 160

Gly Leu Ala Phe Ser Gly Ala Leu Ile Trp Ala Gly Tyr Ser Thr Met
                165                 170                 175

Thr Ala Arg Ile Ala Gln Gly Lys Asn Gly Ile Thr Leu Phe Phe Met
            180                 185                 190

Leu Thr Ala Ala Ala Leu Trp Val Lys Tyr Leu Val Gln Gly Ala Pro
        195                 200                 205

Ala Met Thr Phe Thr Val Pro Ala Leu Val Tyr Leu Leu Leu Ala Ala
    210                 215                 220
```

Met Ala Met Gly Phe Gly Tyr Ala Ala Trp Asn Val Gly Ile Leu His
225                 230                 235                 240

Gly Asn Val Thr Ile Leu Ala Gly Ala Ser Tyr Phe Ile Pro Val Phe
            245                 250                 255

Ser Ala Ala Leu Ser Thr Val Leu Leu Gln Ala Pro Leu Thr Leu Thr
            260                 265                 270

Phe Trp Gln Gly Ser Ser Met Val Cys Leu Gly Ala Leu Leu Cys Trp
        275                 280                 285

Leu Ala Ile Arg Val Arg Lys Pro Arg Ser Leu Lys Ser Ala Ala
    290                 295                 300

<210> SEQ ID NO 15
<211> LENGTH: 912
<212> TYPE: DNA
<213> ORGANISM: Artificial Sequence
<220> FEATURE:
<223> OTHER INFORMATION: Afa NT seq.

<400> SEQUENCE: 15

```
atgaagcaat ctgataaggc aaccctgatc gggctgatcg ccattgtcct ttggagcacg      60
attgtcggcc tgatacgcag cgtcagcgac tctctgggcg taaccggcgg cgctgccctg     120
atttacaccc tggcctcggt cttcttctt ttatcagtgg gctgggtacg cttgcgcgac      180
ttcccgcgtc gctacctgat ctggggcagt gtgctgtttg tctgctatga actctgcctg     240
gccctgtcca tcggctatgc ccacaacagc cagcaggcaa ttgaagtggg gatggtcaac     300
tatctgtggc cgacctttac cattgtggcc gccatcttgt tcaataagca aaaagccaat     360
gggctgcttg cacccggcct gctcttgtcc atgatgggaa tcagctggat ctgggcggc      420
gagcaaggct tgagcctgca caacatctgg ctgaatgtgc aggacaatcc cttgagctac     480
ggcctggcct ttagcggcgc gctgatctgg gccggctaca gcaccatgac cgcccgcatc     540
gcccagggca aaaatggcat caccctgttt ttcatgctga cggcagcggc cttgtgggtg     600
aagtacctgg tccaaggtgc tcctgccatg acgtttacgg ttcccgcctt ggtgtatttg     660
ctgctggcgg ccatggcgat gggctttggc tatgccgcct ggaatgtcgg tatttttgcat    720
ggcaatgtca ccatcctggc cggcgcttcc tactttattc cggtattttc agccgccctg     780
tccaccgttt tgctgcaagc tccgttgacg ctgaccttct ggcaaggctc gtccatggtg     840
tgtttgggtg ccctgctatg ctggctggcc atccgggttc gcaaaccccg gtcactaaaa     900
agcgctgcct ga                                                         912
```

<210> SEQ ID NO 16
<211> LENGTH: 35
<212> TYPE: DNA
<213> ORGANISM: Artificial Sequence
<220> FEATURE:
<223> OTHER INFORMATION: Afa-1

<400> SEQUENCE: 16
tagaggagac acaacatgaa gcaatctgat aaggc      35

<210> SEQ ID NO 17
<211> LENGTH: 35
<212> TYPE: DNA
<213> ORGANISM: Artificial Sequence
<220> FEATURE:
<223> OTHER INFORMATION: Afa-2

<400> SEQUENCE: 17
gctcttcctg tttagttcag gcagcgcttt ttagt                                      35

<210> SEQ ID NO 18
<211> LENGTH: 39
<212> TYPE: DNA
<213> ORGANISM: Artificial Sequence
<220> FEATURE:
<223> OTHER INFORMATION: PgapA(-Afa)-2

<400> SEQUENCE: 18
atcagattgc ttcatgttgt gtctcctcta aagattgta                                  39

<210> SEQ ID NO 19
<211> LENGTH: 314
<212> TYPE: PRT
<213> ORGANISM: Artificial Sequence
<220> FEATURE:
<223> OTHER INFORMATION: Cne AA seq.

<400> SEQUENCE: 19

```
Met Gln Ser Lys Ser Lys Ala Thr Leu Ile Gly Leu Ile Ala Ile Leu
 1               5                  10                  15

Leu Trp Ser Ser Ile Val Gly Leu Ile Arg Gly Val Ser Glu Asn Leu
            20                  25                  30

Gly Ala Thr Gly Gly Ala Ala Met Ile Tyr Thr Val Ala Ser Ala Leu
        35                  40                  45

Leu Leu Leu Thr Val Gly Phe Val Arg Met Gln Asp Phe Pro Arg Arg
    50                  55                  60

Tyr Leu Val Trp Gly Ser Ile Leu Phe Val Ser Tyr Glu Leu Cys Leu
 65                 70                  75                  80

Ser Leu Ser Ile Gly Tyr Ala Asn Ser Ser Arg Gln Ala Ile Glu Val
                85                  90                  95

Gly Met Val Asn Tyr Leu Trp Pro Ser Phe Thr Met Leu Cys Ala Ile
            100                 105                 110

Ala Phe Asn Lys Gln Lys Ala Asn Leu Leu Ile Ile Pro Gly Phe Leu
        115                 120                 125

Ile Ala Ile Leu Gly Ile Cys Trp Val Leu Gly Gly Asp Gln Gly Leu
    130                 135                 140

Asp Phe Ala Gly Met Ala Glu Asn Ile Gln Asp Asn Pro Leu Ser Tyr
145                 150                 155                 160

Gly Leu Ala Phe Leu Gly Ala Leu Ile Trp Ala Ala Tyr Cys Thr Val
                165                 170                 175

Thr Asn Arg Ile Ala Glu Gly Arg Asn Gly Ile Thr Leu Phe Phe Met
            180                 185                 190

Leu Thr Ala Leu Ala Leu Trp Ile Lys Tyr Phe Ala Thr Glu Ser Gly
        195                 200                 205

Ser Met Glu Phe Ser Tyr Gln Ala Val Ile Tyr Leu Ala Leu Ala Ala
    210                 215                 220

Ser Ala Met Gly Phe Gly Tyr Ala Ala Trp Asn Val Gly Ile Leu His
225                 230                 235                 240

Gly Asn Val Thr Val Leu Ala Gly Ala Ser Tyr Phe Ile Pro Val Leu
                245                 250                 255

Ser Ala Ala Leu Ala Ala Met Leu Leu Arg Thr Pro Leu Ser Ile Ala
            260                 265                 270

Phe Trp Lys Gly Ala Ser Met Val Cys Ala Gly Ser Ile Leu Cys Trp
        275                 280                 285
```

Leu Ala Thr Arg Gly Gln Arg Ser Lys Ala Pro Pro Leu Pro Glu Leu
        290                 295                 300

Pro Gln Ser Arg Glu Arg Val Gln Glu Pro
305                 310

<210> SEQ ID NO 20
<211> LENGTH: 945
<212> TYPE: DNA
<213> ORGANISM: Artificial Sequence
<220> FEATURE:
<223> OTHER INFORMATION: Cne NT seq.

<400> SEQUENCE: 20

| | | |
|---|---|---|
| atgcaaagca agagcaaagc aactctcatc gggctcatcg cgattctgtt atggagctcg | 60 |
| attgtcggcc tgattcgcgg tgtcagcgaa aaccttgggg caaccggtgg ggcggcaatg | 120 |
| atctataccg tcgcctcggc cctgctcttg ctgacagtcg gtttcgtcag aatgcaggat | 180 |
| tttccccggc gctatctggt ttggggaagc attctgttcg tttcgtacga gctgtgtctt | 240 |
| tccttgtcca ttggctacgc caacagcagc aggcaagcca ttgaggtggg gatggtcaac | 300 |
| tacttgtggc cgagcttcac catgctgtgt gccatcgcat tcaacaagca gaaggccaac | 360 |
| ttgctgatca ttcccggctt cctgatcgcc attctcggga tctgctgggt gcttggcggg | 420 |
| gatcagggcc tggacttcgc cgggatggcg gagaacatcc aggacaatcc gctcagctat | 480 |
| gggctggcct tccttggtgc cctgatctgg gcggcgtatt gcactgtgac caaccggatt | 540 |
| gccgaaggca ggaatggcat cacgctgttc ttcatgctga cagcgctggc gttgtggatc | 600 |
| aagtatttcg ccacagagag cgggtcgatg gaatttagct atcaggcagt gatttatctt | 660 |
| gcgttggccg cctctgcgat gggattcggc tatgcggcct ggaatgttgg catcctgcat | 720 |
| ggcaatgtca ccgtccttgc cggcgcttcc tacttcattc cggtactttc cgccgccctg | 780 |
| gcggccatgc tcttgcgtac accctgtcg atcgccttct ggaagggcgc atccatggta | 840 |
| tgtgcggggt cgatcctctg ttggctggca acacgtgggc aacgttccaa ggcacctccg | 900 |
| ttgccggaat taccgcagtc gcgcgaacgt gtccaggaac cgtga | 945 |

<210> SEQ ID NO 21
<211> LENGTH: 35
<212> TYPE: DNA
<213> ORGANISM: Artificial Sequence
<220> FEATURE:
<223> OTHER INFORMATION: Cne-1

<400> SEQUENCE: 21
tagaggagac acaacatgca aagcaagagc aaagc         35

<210> SEQ ID NO 22
<211> LENGTH: 35
<212> TYPE: DNA
<213> ORGANISM: Artificial Sequence
<220> FEATURE:
<223> OTHER INFORMATION: Cne-2

<400> SEQUENCE: 22
ggctcttcct gtttagttca cggttcctgg acacg         35

<210> SEQ ID NO 23
<211> LENGTH: 39
<212> TYPE: DNA
<213> ORGANISM: Artificial Sequence
<220> FEATURE:
<223> OTHER INFORMATION: PgapA(-Cne)-2

<400> SEQUENCE: 23
gctcttgctt tgcatgttgt gtctcctcta aagattgta                                    39

<210> SEQ ID NO 24
<211> LENGTH: 293
<212> TYPE: PRT
<213> ORGANISM: Artificial Sequence
<220> FEATURE:
<223> OTHER INFORMATION: Eco AA seq.

<400> SEQUENCE: 24

Met Thr Arg Gln Lys Ala Thr Leu Ile Gly Leu Ile Ala Ile Val Leu
1               5                   10                  15

Trp Ser Thr Met Val Gly Leu Ile Arg Gly Val Ser Glu Gly Leu Gly
                20                  25                  30

Pro Val Gly Gly Ala Ala Ile Tyr Ser Leu Ser Gly Leu Leu Leu
            35                  40                  45

Ile Phe Thr Val Gly Phe Pro Arg Ile Arg Gln Ile Pro Lys Gly Tyr
        50                  55                  60

Leu Leu Ala Gly Ser Leu Leu Phe Val Ser Tyr Glu Ile Cys Leu Ala
65                  70                  75                  80

Leu Ser Leu Gly Tyr Ala Ala Thr His His Gln Ala Ile Glu Val Gly
                85                  90                  95

Met Val Asn Tyr Leu Trp Pro Ser Leu Thr Ile Leu Phe Ala Ile Leu
            100                 105                 110

Phe Asn Gly Gln Lys Thr Asn Trp Leu Ile Val Pro Gly Leu Leu Leu
        115                 120                 125

Ala Leu Val Gly Val Cys Trp Val Leu Gly Gly Asp Asn Gly Leu His
130                 135                 140

Tyr Asp Glu Ile Ile Asn Asn Ile Thr Thr Ser Pro Leu Ser Tyr Phe
145                 150                 155                 160

Leu Ala Phe Ile Gly Ala Phe Ile Trp Ala Ala Tyr Cys Thr Val Thr
                165                 170                 175

Asn Lys Tyr Ala Arg Gly Phe Asn Gly Ile Thr Val Phe Val Leu Leu
            180                 185                 190

Thr Gly Ala Ser Leu Trp Val Tyr Tyr Phe Leu Thr Pro Gln Pro Glu
        195                 200                 205

Met Ile Phe Ser Thr Pro Val Met Ile Lys Leu Ile Ser Ala Ala Phe
    210                 215                 220

Thr Leu Gly Phe Ala Tyr Ala Ala Trp Asn Val Gly Ile Leu His Gly
225                 230                 235                 240

Asn Val Thr Ile Met Ala Val Gly Ser Tyr Phe Thr Pro Val Leu Ser
                245                 250                 255

Ser Ala Leu Ala Ala Val Leu Leu Ser Ala Pro Leu Ser Phe Ser Phe
            260                 265                 270

Trp Gln Gly Ala Leu Met Val Cys Gly Gly Ser Leu Leu Cys Trp Leu
        275                 280                 285

Ala Thr Arg Arg Gly
    290

<210> SEQ ID NO 25
<211> LENGTH: 882
<212> TYPE: DNA
<213> ORGANISM: Artificial Sequence
<220> FEATURE:
<223> OTHER INFORMATION: Eco NT seq.

<400> SEQUENCE: 25

```
atgacacgac aaaaagcaac gctcataggg ctgatagcga tcgtcctgtg gagcacgatg    60
gtaggattga ttcgcggtgt cagtgagggg ctcggcccgg tcggcggcgc agctgctatc   120
tattcattaa gcgggctgct gttaatcttc acggttggat ttccgcgtat tcggcaaatc   180
ccgaaaggct atttactcgc cgggagtctg ttattcgtca gctatgaaat ctgtctggcg   240
ctttccttag ggtatgcggc gacccatcat caggcgattg aagtgggtat ggtgaactat   300
ctgtggccca gcctgacaat tctctttgcc attctgttta atggtcagaa aaccaactgg   360
ttgattgtac ctggattatt attagccctc gtcggcgtct gttgggtgtt aggcggtgac   420
aatgggttac attatgatga aatcatcaat aatatcacca ccagcccatt gagttatttc   480
ctggcgttca ttggtgcgtt tatctgggca gcctattgca cagtaacgaa taaatacgca   540
cgcggattta atggaattac cgttttttgtc ctgctaacgg gagcaagtct gtgggtttac   600
tattttctta cgccacaacc agaaatgata tttagcacgc ccgtcatgat taaactcatc   660
tctgcggcat ttaccttagg atttgcttat gctgcatgga atgtcggtat attgcatggc   720
aatgtcacca ttatggcggt aggttcgtat tttacgcctg tactttcctc agcgcttgca   780
gccgtgctgc tcagcgcccc gctgtcgttc tcgttctggc aaggcgcgct gatggtctgc   840
ggcggttccc tgctctgctg gctggcgaca cgtcgtggtt aa                     882
```

<210> SEQ ID NO 26
<211> LENGTH: 35
<212> TYPE: DNA
<213> ORGANISM: Artificial Sequence
<220> FEATURE:
<223> OTHER INFORMATION: Eco-1

<400> SEQUENCE: 26

```
tagaggagac acaacatgac acgacaaaaa gcaac                               35
```

<210> SEQ ID NO 27
<211> LENGTH: 35
<212> TYPE: DNA
<213> ORGANISM: Artificial Sequence
<220> FEATURE:
<223> OTHER INFORMATION: Eco-2

<400> SEQUENCE: 27

```
gctcttcctg tttagtttaa ccacgacgtg tcgcc                               35
```

<210> SEQ ID NO 28
<211> LENGTH: 37
<212> TYPE: DNA
<213> ORGANISM: Artificial Sequence
<220> FEATURE:
<223> OTHER INFORMATION: PgapA(-Eco)-2

<400> SEQUENCE: 28

```
tttttgtcgt gtcatgttgt gtctcctcta aagattg                             37
```

<210> SEQ ID NO 29
<211> LENGTH: 35
<212> TYPE: DNA
<213> ORGANISM: Artificial Sequence
<220> FEATURE:
<223> OTHER INFORMATION: Hrh-3

<400> SEQUENCE: 29

```
atagagagtg actcaatgaa tagcaagaag gccac                               35
```

```
<210> SEQ ID NO 30
<211> LENGTH: 33
<212> TYPE: DNA
<213> ORGANISM: Artificial Sequence
<220> FEATURE:
<223> OTHER INFORMATION: Hrh-4

<400> SEQUENCE: 30
tcgagctcgg taccectaca aacagtccgc cac                                33

<210> SEQ ID NO 31
<211> LENGTH: 34
<212> TYPE: DNA
<213> ORGANISM: Artificial Sequence
<220> FEATURE:
<223> OTHER INFORMATION: PyccA - 1

<400> SEQUENCE: 31
ctctagagga tccccttcca gatcaaatgc gtaa                               34

<210> SEQ ID NO 32
<211> LENGTH: 35
<212> TYPE: DNA
<213> ORGANISM: Artificial Sequence
<220> FEATURE:
<223> OTHER INFORMATION: PyccA(-Hrh)-2

<400> SEQUENCE: 32
cttcttgcta ttcattgagt cactctctat gacag                              35

<210> SEQ ID NO 33
<211> LENGTH: 35
<212> TYPE: DNA
<213> ORGANISM: Artificial Sequence
<220> FEATURE:
<223> OTHER INFORMATION: Pst-3

<400> SEQUENCE: 33
atagagagtg actcaatgaa aaccagcgt aaagc                               35

<210> SEQ ID NO 34
<211> LENGTH: 33
<212> TYPE: DNA
<213> ORGANISM: Artificial Sequence
<220> FEATURE:
<223> OTHER INFORMATION: Pst-4

<400> SEQUENCE: 34
tcgagctcgg tacccttatc cgtttcgacg cgg                                33

<210> SEQ ID NO 35
<211> LENGTH: 35
<212> TYPE: DNA
<213> ORGANISM: Artificial Sequence
<220> FEATURE:
<223> OTHER INFORMATION: PyccA(-Pst)-2

<400> SEQUENCE: 35
acgctggttt ttcattgagt cactctctat gacag                              35

<210> SEQ ID NO 36
<211> LENGTH: 35
<212> TYPE: DNA
<213> ORGANISM: Artificial Sequence
<220> FEATURE:
<223> OTHER INFORMATION: Afa-3
```

```
<400> SEQUENCE: 36
atagagagtg actcaatgaa gcaatctgat aaggc                                35

<210> SEQ ID NO 37
<211> LENGTH: 34
<212> TYPE: DNA
<213> ORGANISM: Artificial Sequence
<220> FEATURE:
<223> OTHER INFORMATION: Afa-4

<400> SEQUENCE: 37
tcgagctcgg taccctcagg cagcgctttt tagt                                 34

<210> SEQ ID NO 38
<211> LENGTH: 35
<212> TYPE: DNA
<213> ORGANISM: Artificial Sequence
<220> FEATURE:
<223> OTHER INFORMATION: PyccA(-Afa)-2

<400> SEQUENCE: 38
atcagattgc ttcattgagt cactctctat gacag                                35

<210> SEQ ID NO 39
<211> LENGTH: 35
<212> TYPE: DNA
<213> ORGANISM: Artificial Sequence
<220> FEATURE:
<223> OTHER INFORMATION: Cne-3

<400> SEQUENCE: 39
atagagagtg actcaatgca aagcaagagc aaagc                                35

<210> SEQ ID NO 40
<211> LENGTH: 33
<212> TYPE: DNA
<213> ORGANISM: Artificial Sequence
<220> FEATURE:
<223> OTHER INFORMATION: Cne-4

<400> SEQUENCE: 40
tcgagctcgg taccctcacg gttcctggac acg                                  33

<210> SEQ ID NO 41
<211> LENGTH: 35
<212> TYPE: DNA
<213> ORGANISM: Artificial Sequence
<220> FEATURE:
<223> OTHER INFORMATION: PyccA(-Cne)-2

<400> SEQUENCE: 41
gctcttgctt tgcattgagt cactctctat gacag                                35

<210> SEQ ID NO 42
<211> LENGTH: 35
<212> TYPE: DNA
<213> ORGANISM: Artificial Sequence
<220> FEATURE:
<223> OTHER INFORMATION: Eco-3

<400> SEQUENCE: 42
atagagagtg actcaatgac acgacaaaaa gcaac                                35
```

```
<210> SEQ ID NO 43
<211> LENGTH: 34
<212> TYPE: DNA
<213> ORGANISM: Artificial Sequence
<220> FEATURE:
<223> OTHER INFORMATION: Eco-4

<400> SEQUENCE: 43
tcgagctcgg taccettaac cacgacgtgt cgcc                               34

<210> SEQ ID NO 44
<211> LENGTH: 35
<212> TYPE: DNA
<213> ORGANISM: Artificial Sequence
<220> FEATURE:
<223> OTHER INFORMATION: PyccA(-Eco)-2

<400> SEQUENCE: 44
tttttgtcgt gtcattgagt cactctctat gacag                              35

<210> SEQ ID NO 45
<211> LENGTH: 35
<212> TYPE: DNA
<213> ORGANISM: Artificial Sequence
<220> FEATURE:
<223> OTHER INFORMATION: Pspl7-trpE(S38R)_L-1

<400> SEQUENCE: 45
tcgagctcgg tacccaaaca actgcgacgt gtgtc                              35

<210> SEQ ID NO 46
<211> LENGTH: 35
<212> TYPE: DNA
<213> ORGANISM: Artificial Sequence
<220> FEATURE:
<223> OTHER INFORMATION: Pspl7-trpE(S38R)_L-2

<400> SEQUENCE: 46
catgaagcgc cggtacctta atcattttg ggttc                               35

<210> SEQ ID NO 47
<211> LENGTH: 35
<212> TYPE: DNA
<213> ORGANISM: Artificial Sequence
<220> FEATURE:
<223> OTHER INFORMATION: Pspl7-trpE(S38R)_R-1

<400> SEQUENCE: 47
gccctgttgg aacgcgctga tatcaccacc aagaa                              35

<210> SEQ ID NO 48
<211> LENGTH: 35
<212> TYPE: DNA
<213> ORGANISM: Artificial Sequence
<220> FEATURE:
<223> OTHER INFORMATION: Pspl7-trpE(S38R)_R-2

<400> SEQUENCE: 48
ctctagagga tccccagatg tcaccgttgt aaatg                              35

<210> SEQ ID NO 49
<211> LENGTH: 294
<212> TYPE: DNA
<213> ORGANISM: Artificial Sequence
<220> FEATURE:
<223> OTHER INFORMATION: spl7 promoter seq.
```

<400> SEQUENCE: 49

```
ggcgcttcat gtcaacaatc tttaacgttt tcaagttcac aagtcgtgtt caaatggtga      60
caagattgga cactgtgctg aattggcacc aagccctcat aaatgataga tctaaatcga     120
atatcaatat atggtctgtt tattggaacg cgtcccagtg gctgagacgc atccgctaaa     180
gccccaggaa ccctgtgcag aaagaacaaa taatcgtgaa ttttggcagc aacagcaatt     240
cctgctacaa ttgaaaacgt gcaaaagcat agattattgg aggagatcaa aaca           294
```

<210> SEQ ID NO 50
<211> LENGTH: 35
<212> TYPE: DNA
<213> ORGANISM: Artificial Sequence
<220> FEATURE:
<223> OTHER INFORMATION: Pspl7 - 1

<400> SEQUENCE: 50

```
cccaaaaatg attaaggtac cggcgcttca tgtca                                 35
```

<210> SEQ ID NO 51
<211> LENGTH: 37
<212> TYPE: DNA
<213> ORGANISM: Artificial Sequence
<220> FEATURE:
<223> OTHER INFORMATION: Pspl7 - 2

<400> SEQUENCE: 51

```
gggattcgtg ctcatgatat ctgttttgat ctcctcc                               37
```

<210> SEQ ID NO 52
<211> LENGTH: 35
<212> TYPE: DNA
<213> ORGANISM: Artificial Sequence
<220> FEATURE:
<223> OTHER INFORMATION: trpE (S38R) - 1

<400> SEQUENCE: 52

```
atcaaaacag atatcatgag cacgaatccc catgt                                 35
```

<210> SEQ ID NO 53
<211> LENGTH: 35
<212> TYPE: DNA
<213> ORGANISM: Artificial Sequence
<220> FEATURE:
<223> OTHER INFORMATION: trpE (S38R) - 2

<400> SEQUENCE: 53

```
gtggtgatat cagcgcgttc aacagggct gcatc                                  35
```

<210> SEQ ID NO 54
<211> LENGTH: 19
<212> TYPE: DNA
<213> ORGANISM: Artificial Sequence
<220> FEATURE:
<223> OTHER INFORMATION: Confirm_Pspl7-trpE(S38R) - 1

<400> SEQUENCE: 54

```
gaagaagagg ctgcagatg                                                   19
```

<210> SEQ ID NO 55
<211> LENGTH: 18
<212> TYPE: DNA
<213> ORGANISM: Artificial Sequence
<220> FEATURE:
<223> OTHER INFORMATION: Confirm_Psp17-trpE(S38R) - 2

<400> SEQUENCE: 55
gatcagcgcc atcatgtt                                                  18

<210> SEQ ID NO 56
<211> LENGTH: 35
<212> TYPE: DNA
<213> ORGANISM: Artificial Sequence
<220> FEATURE:
<223> OTHER INFORMATION: Pn-tkt_L - 1

<400> SEQUENCE: 56
tcgagctcgg tacccaaact ttgagtgggt gcgtg                               35

<210> SEQ ID NO 57
<211> LENGTH: 35
<212> TYPE: DNA
<213> ORGANISM: Artificial Sequence
<220> FEATURE:
<223> OTHER INFORMATION: Pn-tkt_L - 2

<400> SEQUENCE: 57
tcgagctacg agggcggttc ccagcccttc attag                               35

<210> SEQ ID NO 58
<211> LENGTH: 35
<212> TYPE: DNA
<213> ORGANISM: Artificial Sequence
<220> FEATURE:
<223> OTHER INFORMATION: Pn-tkt_R - 1

<400> SEQUENCE: 58
attaacggtt aattgattct ggacgtcatg actac                               35

<210> SEQ ID NO 59
<211> LENGTH: 35
<212> TYPE: DNA
<213> ORGANISM: Artificial Sequence
<220> FEATURE:
<223> OTHER INFORMATION: Pn-tkt_R - 2

<400> SEQUENCE: 59
ctctagagga tccccgcctc gatgatgcag tcgtc                               35

<210> SEQ ID NO 60
<211> LENGTH: 35
<212> TYPE: DNA
<213> ORGANISM: Artificial Sequence
<220> FEATURE:
<223> OTHER INFORMATION: Pn-tkt - 1

<400> SEQUENCE: 60
gaagggctgg gaaccgccct cgtagctcga gagtt                               35

<210> SEQ ID NO 61
<211> LENGTH: 37
<212> TYPE: DNA
<213> ORGANISM: Artificial Sequence
<220> FEATURE:
<223> OTHER INFORMATION: Pn-tkt - 2

<400> SEQUENCE: 61
catgacgtcc agaatcaatt aaccgttaat ggagtcc                             37

-continued

```
<210> SEQ ID NO 62
<211> LENGTH: 20
<212> TYPE: DNA
<213> ORGANISM: Artificial Sequence
<220> FEATURE:
<223> OTHER INFORMATION: Confirm_Pn-tkt - 1

<400> SEQUENCE: 62
acccagaacc ccaaattttc                                               20

<210> SEQ ID NO 63
<211> LENGTH: 19
<212> TYPE: DNA
<213> ORGANISM: Artificial Sequence
<220> FEATURE:
<223> OTHER INFORMATION: Confirm_Pn-tkt - 2

<400> SEQUENCE: 63
ttgagttcga caactttgg                                                19

<210> SEQ ID NO 64
<211> LENGTH: 70
<212> TYPE: DNA
<213> ORGANISM: Artificial Sequence
<220> FEATURE:
<223> OTHER INFORMATION: primer

<400> SEQUENCE: 64
tgcaatgcat aacaacgcag tcgcactatt tttcactgga gagaagccct gtgtaggctg   60
gagctgcttc                                                          70

<210> SEQ ID NO 65
<211> LENGTH: 70
<212> TYPE: DNA
<213> ORGANISM: Artificial Sequence
<220> FEATURE:
<223> OTHER INFORMATION: primer

<400> SEQUENCE: 65
tgcaatgcat aacaacgcag tcgcactatt tttcactgga gagaagccct gtccatatga   60
atatcctcct                                                          70

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gggcaggatc tcctgtcatc                                               20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
aaatgtcgga taaggcaccg                                               20
```

```
<210> SEQ ID NO 68
<211> LENGTH: 70
<212> TYPE: DNA
<213> ORGANISM: Artificial Sequence
<220> FEATURE:
<223> OTHER INFORMATION: primer

<400> SEQUENCE: 68
tgtaatattc acagggatca ctgtaattaa aataaatgaa ggattatgta gtgtaggctg      60
gagctgcttc                                                            70

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
tgtagggtaa gagagtggct aacatcctta tagccactct gtagtattaa gtccatatga      60
atatcctcct                                                            70

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
acatccttat agccactctg                                                 20

<210> SEQ ID NO 71
<211> LENGTH: 70
<212> TYPE: DNA
<213> ORGANISM: Artificial Sequence
<220> FEATURE:
<223> OTHER INFORMATION: primer

<400> SEQUENCE: 71
tacaaccggg ggaggcattt tgcttccccc gctaacaatg gcgacatatt gtgtaggctg      60
gagctgcttc                                                            70

<210> SEQ ID NO 72
<211> LENGTH: 70
<212> TYPE: DNA
<213> ORGANISM: Artificial Sequence
<220> FEATURE:
<223> OTHER INFORMATION: primer

<400> SEQUENCE: 72
gcattcggtg cacgatgcct gatgcgccac gtcttatcag gcctacaaaa gtccatatga      60
atatcctcct                                                            70

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
aggacggata aggcgttcac                                                 20
```

```
<210> SEQ ID NO 74
<211> LENGTH: 26
<212> TYPE: DNA
<213> ORGANISM: Artificial Sequence
<220> FEATURE:
<223> OTHER INFORMATION: trpE - 1

<400> SEQUENCE: 74
gaattcatgc aaacacaaaa accgac                                              26

<210> SEQ ID NO 75
<211> LENGTH: 25
<212> TYPE: DNA
<213> ORGANISM: Artificial Sequence
<220> FEATURE:
<223> OTHER INFORMATION: trpE - 2

<400> SEQUENCE: 75
gaattctcag aaagtctcct gtgca                                               25

<210> SEQ ID NO 76
<211> LENGTH: 37
<212> TYPE: DNA
<213> ORGANISM: Artificial Sequence
<220> FEATURE:
<223> OTHER INFORMATION: trpE(P21S) - 1

<400> SEQUENCE: 76
cgcttatcgc gacaattcca ccgcgctttt tcaccag                                  37

<210> SEQ ID NO 77
<211> LENGTH: 37
<212> TYPE: DNA
<213> ORGANISM: Artificial Sequence
<220> FEATURE:
<223> OTHER INFORMATION: trpE(P21S) - 2

<400> SEQUENCE: 77
ctggtgaaaa agcgcggtgg aattgtcgcg ataagcg                                  37
```

L-TRYPTOPHAN EXPORTER AND METHOD OF PRODUCING L-TRYPTOPHAN USING THE SAME

CROSS-REFERENCE TO RELATED APPLICATIONS

This application is a U.S. National Stage application of PCT/KR2019/002238 filed 22 Feb. 2019, which claims priority to Korean Patent Application No. 10-2018-0022054 filed 23 Feb. 2018, the entire disclosures of which are herein incorporated by reference.

SEQUENCE LISTING

The instant application contains a Sequence Listing which has been submitted electronically in ASCII format and is hereby incorporated by reference in its entirety. Said ASCII copy, created on 4 Oct. 2019, is named OPA18282_ST25.txt and is 33 Kilobytes in size.

TECHNICAL FIELD

The present disclosure relates to a microorganism producing L-tryptophan, in which the microorganism is modified such that a protein having tryptophan-exporting activity is expressed, and a method for producing L-tryptophan using the microorganism.

BACKGROUND ART

L-Tryptophan, an essential amino acid, has been widely used as a raw material for feed additives, medicines (e.g., infusion solutions), health food materials, etc. At present, a direct fermentation method using a microorganism is mainly used for the production of L-tryptophan.

Previously, the microorganisms that had mainly been used in the production of L-tryptophan were selected strains exhibiting resistance to analogs through chemical or physical mutation. However, the rapid development of genetic recombination technology and identification of molecular-level regulatory mechanisms in the 1990s has enabled the use of recombinant strains using genetic engineering techniques.

Meanwhile, the expression of a gene capable of exporting a particular amino acid has contributed to an increase in productivity of the corresponding amino acid in microorganisms. The enhancement of the L-lysine-exporting gene (lysE) in a microorganism of the genus *Corynebacterium* has improved the productivity of lysine (WO 9723597A2). Additionally, the enhancement of the rhtC gene in *E. coli* has improved the resistance to L-threonine, and simultaneously, has also improved the productivity of L-homoserine, L-threonine, and L-leucine (EP1013765A1). EP1016710B1 discloses that the improvement of the productivity of L-glutamic acid, L-lysine, L-threonine, L-alanine, L-histidine, L-proline, L-arginine, L-valine, and L-isoleucine by enhancing yahN, yeaS, yfiK, and yggA genes, whose functions are not yet identified in *E. coli*.

However, no exporting protein showing specificity to L-tryptophan has yet been reported. Although the yddG gene of *E. coli* is known, it shows higher specificity to L-phenylalanine than to L-tryptophan (*FEMS Microbiol Lett* 275 (2007) 312 to 318). Additionally, in a microorganism of the genus *Corynebacterium* which is mainly used as a strain producing L-amino acid fermentation, no protein that can export L-tryptophan or an aromatic amino acid has been reported (*J Ind Microbiol Biotechnol.* 2015 May; 42(5): 787 to 97).

Under the circumstances, the inventors of the present disclosure have succeeded in expressing a novel tryptophan-exporting protein having specificity to L-tryptophan in an L-tryptophan-producing microorganism and have discovered that the amount of L-tryptophan production was significantly improved, thereby completing the present disclosure.

DISCLOSURE

Technical Problem

An object of the present disclosure is to provide a microorganism producing L-tryptophan, in which the microorganism is modified such that a protein having an L-tryptophan-exporting activity is expressed.

Another object of the present disclosure is to provide a method which includes culturing the microorganism in a medium; and recovering L-tryptophan from the cultured microorganism or the medium.

Still another object of the present disclosure is to provide a vector comprising a polynucleotide encoding a novel protein having an L-tryptophan-exporting activity, comprising the amino acid sequence of SEQ ID NO: 1.

Still another object of the present disclosure is to provide a method for increasing an L-tryptophan-exporting activity of a microorganism, comprising modifying a microorganism such that a protein having an L-tryptophan-exporting activity comprising the amino acid sequence of SEQ ID NO: 1 is expressed in the microorganism.

Technical Solution

Hereinbelow, exemplary embodiments of the present disclosure will be described in detail. Meanwhile, each of the explanations and exemplary embodiments disclosed herein can be applied to other explanations and exemplary embodiments. That is, all of the combinations of various factors disclosed herein belong to the scope of the present disclosure. Furthermore, the scope of the present disclosure should not be limited by the specific disclosure provided hereinbelow.

To achieve the above objects, an aspect of the present disclosure relates to a microorganism producing L-tryptophan, in which the microorganism is modified such that a protein having an L-tryptophan-exporting activity comprising the amino acid sequence of SEQ ID NO: 1 is expressed.

As used herein, the term "L-tryptophan", an α-amino acid, refers to an essential amino acid not synthesized in vivo and it refers to an aromatic L-amino acid having a chemical formula of $C_{11}H_{12}N_2O_2$.

In the present disclosure, "protein having an L-tryptophan-exporting activity" refers to a membrane protein which has an activity of specifically exporting L-tryptophan from a cell.

The protein having an L-tryptophan-exporting activity may be, for example, a protein including the amino acid sequence of SEQ ID NO: 1. The protein including the amino acid sequence of SEQ ID NO: 1 may be used interchangeably with a protein having the amino acid sequence of SEQ ID NO: 1 and a protein consisting of the amino acid sequence of SEQ ID NO: 1.

Specifically, in the present disclosure, the protein having an L-tryptophan-exporting activity including the amino acid sequence of SEQ ID NO: 1 refers to a protein having an L-tryptophan-exporting activity among the proteins derived from *Herbaspirillum rhizosphaerae*. In particular, "*Herbaspirillum rhizosphaerae*" is a gram negative bacterium belonging to the genus *Herbaspirillum*. In Korea, it can be isolated from the rhizosphere in the soil, as a strain isolated from Ulleung island, etc.

Additionally, although the protein having an L-tryptophan-exporting activity of the present disclosure was defined as a protein including the amino acid sequence of SEQ ID NO: 1, it does not exclude an addition of a sequence upstream or downstream of the amino acid sequence of SEQ ID NO: 1, a mutation that may occur naturally, or a silent mutation thereof, and when the protein has an activity identical or corresponding to the protein including the amino acid sequence of SEQ ID NO: 1, it is apparent to those skilled in the art that the protein belongs to the protein having an L-tryptophan-exporting activity of the present disclosure. For example, the protein having an L-tryptophan-exporting activity of the present disclosure may be a protein consisting of the amino acid sequence of SEQ ID NO: 1, or an amino acid sequence having a homology to the amino acid sequence of SEQ ID NO: 1 of 80%, 90%, 95%, 97%, or higher. Additionally, it is apparent that any protein having an amino acid sequence with deletion, modification, substitution, or addition in part of the sequence can also belong to the scope of the present disclosure as long as the protein has an amino acid sequence with any of the above homologies and exhibits an effect corresponding to the above protein.

The term "homology" refers to a percentage of identity between two polynucleotides or polynucleotide moieties (i.e., a degree of matching with a given amino acid sequence or nucleotide sequence) and it may be expressed as a percentage. In the present disclosure, a homologous sequence having an activity identical or similar to a given amino acid or nucleotide sequence is represented as "% homology". The homology between sequences from a moiety to another moiety may be determined by a technique known in the art. For example, homology may be identified using standard software, specifically BLAST 2.0, for calculating parameters such as score, identity, and similarity or by comparing sequences through Southern hybridization under defined stringent conditions. Appropriate hybridization conditions may be defined within the scope of the art and may be determined by a method well known to those skilled in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

Any gene encoding the protein having an L-tryptophan-exporting activity derived from *Herbaspirillum rhizosphaerae* can be included without limitation as long as the gene comprises a sequence that encodes the protein. Specifically, any sequence that can encode the protein having an L-tryptophan-exporting activity comprising the amino acid sequence of SEQ ID NO: 1 can be included without limitation. More specifically, the sequence may be a polynucleotide comprising the polynucleotide sequence of SEQ ID NO: 2. The polynucleotide comprising the polynucleotide sequence of SEQ ID NO: 2 may be interchangeable used with a polynucleotide having the polynucleotide sequence of SEQ ID NO: 2 and a polynucleotide consisting of the polynucleotide sequence of SEQ ID NO: 2.

Additionally, various modifications may be performed in the coding region of the polynucleotide encoding the protein considering codon degeneracy and the codons preferred in a bioorganism where the protein is to be expressed, within the scope not altering the amino acid sequence of the protein. Meanwhile, the polynucleotide encoding the protein may be a polynucleotide having a homology to the polynucleotide sequence of SEQ ID NO: 2 of 80%, 90%, 95%, 97%, or higher. Additionally, it is apparent that any polynucleotide sequence with deletion, modification, substitution, or addition in part of the sequence can also be included within the scope of the present disclosure, as long as the polynucleotide sequence has a homology described above and exhibits an effect identical or corresponding to that of the protein. Alternatively, any probe that can be prepared from known gene sequences (e.g., by hybridizing under stringent conditions with complementary sequences to all or part of the above polynucleotide sequence) and any sequence which encodes a protein having an activity identical or corresponding to that of a protein consisting of the amino acid sequence of SEQ ID NO: 1 can be included without limitation. The term "stringent conditions" refers to conditions which enables specific hybridization between polynucleotides. Such conditions are specifically described in references (e.g., J Sambrook et al., supra). For example, the conditions may include performing hybridization between genes having a high homology, a homology of 80% or higher, specifically 90% or higher, more specifically 95% or higher, even more specifically 97% or higher, and most specifically 99% or higher, while not performing hybridization between genes having a homology of lower than the homologies described above; or performing hybridization once, specifically two or three times, under conventional washing conditions for southern hybridization at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS. Hybridization requires that two nucleic acids contain complementary sequences, although mismatches between bases are possible depending on the stringency of the hybridization. The term "complementary" is used to describe the relationship between mutually hybridizable nucleotide bases. For example, with respect to DNA, adenosine is complementary to thymine, and cytosine is complementary to guanine. Accordingly, the present disclosure may also include isolated nucleic acid fragments complementary to the entire sequence as well as substantially similar nucleotide sequences. Specifically, polynucleotides having a homology can be detected at a $T_m$ value of 55° C. using hybridization conditions that include a hybridization step and using the conditions described above. Additionally, the $T_m$ value may be 60° C., 63° C., or 65° C., but the temperature is not limited thereto and may be appropriately adjusted by those skilled in the art according to the intended purpose. The stringency suitable for the hybridization of polynucleotides depends on the length and degree of complementarity of the polynucleotides, and the related variables are well known in the art (see Sambrook et al., supra, 9.50 to 9.51 and 11.7 to 11.8).

As used herein, the term "to be expressed/being expressed" refers to a state in which a target protein is introduced into a microorganism or, in the case where the protein is present in the microorganism, the activity of the protein is enhanced compared to the activity of its endogenous protein or that before its modification.

Specifically, the term "introduction of a protein" means that a microorganism exhibits the activity of a particular protein which was not originally possessed therein, or the microorganism exhibits enhanced activity compared to its endogenous activity or the activity of the protein before modification. For example, it may mean that a polynucleotide encoding a specific protein is introduced into a chromosome of the microorganism or a vector containing a polynucleotide encoding a specific protein is introduced into a microorganism and thereby exhibits its activity. Additionally, the term "enhancement of activity" means that the activity of a particular protein is improved compared to its endogenous activity or the activity before its modification. The term "endogenous protein" refers to the activity of a particular protein originally possessed by a parent strain of a microorganism, when a trait of a microorganism is altered due to genetic modification caused by a natural or artificial factor.

Specifically, in the present disclosure, the enhancement of activity may be achieved by one or more of the following methods: a method of increasing the intracellular copy number of a gene encoding the protein having an L-tryptophan-exporting activity; a method of introducing modification to the expression control sequence of a gene on the chromosome encoding the protein having an L-tryptophan-exporting activity; a method of replacing the expression control sequence of a gene encoding the protein having an L-tryptophan-exporting activity on the chromosome with a sequence having strong activity; a method of replacing the gene encoding the protein having an L-tryptophan-exporting activity on the chromosome with a gene which is mutated such that the activity of the protein having an L-tryptophan-exporting activity is increased; and a method of introducing modification to a gene encoding the protein having an L-tryptophan-exporting activity on the chromosome such that the activity of the protein having an L-tryptophan-exporting activity is enhanced.

In the above, the method of increasing the copy number of a gene may be performed in a form where the gene is operably linked to a vector or by inserting the gene into the chromosome of a host cell, but the method is not particularly limited thereto. Specifically, the copy number of a gene may be increased by introducing a vector into a host cell, where the vector is operably linked to a polynucleotide encoding the protein of the present disclosure and is able to replicate and function regardless of the host cell. Alternatively, the method of increasing the copy number of a gene may be performed by introducing the vector, which is able to insert the polynucleotide into the chromosome and operably linked to the polynucleotide, into the chromosome of a host cell. The insertion of the polynucleotide into the chromosome may be achieved by a method known in the art (e.g., homologous recombination).

Then, to increase the expression of a polynucleotide, the expression control sequence may be modified by inducing modification therein by deletion, insertion, non-conservative or conservative substitution, or a combination thereof so as to further enhance the activity of the expression control sequence; or by replacing the expression control sequence with a nucleic acid sequence with stronger activity, but the method of modification is not particularly limited thereto. The expression control sequence may include a promoter, an operator sequence, a sequence encoding a ribosome-binding region, spacer, and sequences controlling the termination of transcription and translation, but is not limited thereto.

A strong promoter may be linked to the upstream region of the expression unit of the polynucleotide instead of the original promoter, but is not limited thereto. Examples of strong promoters known in the art may include cj1 to cj7 promoters (KR Patent No. 10-0620092), lac promoter, trp promoter, trc promoter, tac promoter, lambda phage PR promoter, $P_L$ promoter, tet promoter, gapA promoter, SPL7 promoter, SPL13 (sm3) promoter (KR Patent No. 10-1783170), O2 promoter (KR Patent No. 10-1632642), tkt promoter, yccA promoter, etc., but the promoters are not limited thereto.

Further, the polynucleotide sequence on the chromosome may be modified by inducing modification on the expression control sequence by deletion, insertion, non-conservative or conservative substitution, or a combination thereof so as to further enhance the activity of the polynucleotide sequence; or by replacing the polynucleotide sequence with a polynucleotide sequence modified to have stronger activity, but the method of modification is not particularly limited thereto.

The introduction and enhancement of protein activity as described above may generally increase the activity or concentration of the corresponding protein by at least 1%, at least 10%, at least 25%, at least 50%, at least 75%, at least 100%, at least 150%, at least 200%, at least 300%, at least 400%, or at least 500%, and at most 1,000% or 2,000%, based on the activity or concentration of the protein in a wild-type or non-modified microorganism strain, but the range is not limited thereto.

Another aspect of the present disclosure provides a polynucleotide encoding a novel protein having an L-tryptophan-exporting activity, comprising the amino acid sequence of SEQ ID NO: 1, or a vector comprising the polynucleotide.

As used herein, the term "polynucleotide" refers to a DNA or RNA strand having more than a certain length as a nucleotide polymer which is a long chain of nucleotide monomers connected by a covalent bond.

As used herein, the term "vector" refers to a DNA construct comprising the nucleotide sequence of the polynucleotide encoding a target protein, in which the target protein is operably linked to a suitable control sequence so that it can be expressed in an appropriate host. The control sequence includes a promoter capable of initiating transcription, any operator sequence for the control of the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present disclosure is not particularly limited, as long as it is able to replicate in a host cell, and any vector known in the art may be used. Examples of conventional vectors may include a natural or recombinant plasmid, cosmid, virus, and bacteriophage. For example, pWE15, M13, MBL3, MBL4, IXII, ASHII, APII, t10, t11, Charon4A, Charon21A, etc. may be used as a phage vector or cosmid vector; and those based on pBR, pUC, pBluescriptII, pGEM, pTZ, pCL, pET, etc. may be used may be used as a plasmid vector. Specifically, vectors pDZ, pACYC177, pACYC184, pCL, pECCG117, pUC19, pBR322, pMW118, pCC1BAC, etc. may be used.

For example, the polynucleotide encoding the target protein in the chromosome may be replaced with a variant polynucleotide via a vector for chromosomal insertion in a cell. The insertion of the polynucleotide into the chromosome may be performed using any method known in the art, e.g., by homologous recombination, but the method is not limited thereto. A selection marker for confirming the successful insertion of the vector into the chromosome may be further included. The selection marker is used for selection of cells transformed with the vector, i.e., in order to confirm whether the target nucleic acid molecule has been successfully inserted, and markers capable of providing selectable phenotypes (e.g., drug resistance, auxotrophy, resistance to cytotoxic agents, and expression of surface proteins) may be used. Under the circumstances where selective agents are treated, only the cells capable of expressing the selection markers can survive or express other phenotypic traits, and thus the transformed cells can easily be selected.

As used herein, the term "microorganism producing L-tryptophan" refers to a microorganism which can produce L-tryptophan from carbon sources in a medium in an excess amount compared to that of a wild-type or non-modified microorganism strain. Additionally, the microorganism producing L-tryptophan may be a recombinant microorganism. Specifically, the microorganism may be a microorganism of the genus *Enterobacter*, a microorganism of the genus *Escherichia*, a microorganism of the genus *Erwinia*, a microorganism of the genus *Serratia*, a microorganism of the genus *Providencia*, a microorganism of the genus *Corynebacterium*, or a microorganism of the genus *Brevibacterium*, but the type of the microorganism is not particularly limited as long as the microorganism produces L-tryptophan. More specifically, the microorganism may be a microorganism of the genus *Corynebacterium* or a microorganism of the genus *Escherichia*, and even more specifically, the microorganism of the genus *Escherichia* may be *Escherichia coli* and the microorganism of the genus *Corynebacterium* may be *Corynebacterium glutamicum*, but the microorganism of the genus *Corynebacterium* or the genus *Corynebacterium*, in which a protein having an L-tryptophan-exporting activity is introduced or the activity is enhanced and thus the amount of L-tryptophan production can be increased, can be included without limitation.

In the microorganisms described above, the amount of L-tryptophan production may be increased using a method of increasing L-tryptophan biosynthesis by enhancing the expression of tktA gene or blocking branched pathways in the L-tryptophan biosynthesis pathway for the continuous supply of precursors (e.g., erythrose-4-phosphate (E4P)) and efficient energy utilization; or a method of using a lesser amount of ATP, etc.

Specifically, in the present disclosure, the parent strain of the microorganism producing L-tryptophan, in which the microorganism is modified such that the protein having an L-tryptophan-exporting activity is expressed, is not particularly limited as long as the microorganism produces L-tryptophan. The microorganism producing L-tryptophan may be a microorganism in which the activity of a gene in a competitive pathway, a regulator in a directional pathway of L-tryptophan operon, or a gene for introducing and decomposing L-tryptophan is weakened or inactivated so as to enhance the L-tryptophan biosynthesis pathway; and/or the activity of L-tryptophan operon is overexpressed. Specifically, the activity of trpR, a gene for regulating an enzyme group of tryptophan synthesis that inhibits the expression of L-tryptophan biosynthesis genes (trpEDCBA), or Mtr (i.e., a membrane protein) that imports extracellular L-tryptophan into a cell, may be weakened or removed compared to their endogenous activity.

To achieve the above object, another aspect of the present disclosure provides a method for producing L-tryptophan, which includes culturing a microorganism producing L-tryptophan in a medium, in which the microorganism is modified such that a protein having an L-tryptophan-exporting activity comprising the amino acid sequence of SEQ ID NO: 1 is expressed; and recovering the L-tryptophan from the cultured microorganism or the medium.

The L-tryptophan, protein having an L-tryptophan-exporting activity comprising the amino acid sequence of SEQ ID NO: 1, expression of the protein, and microorganism are the same as explained above.

As used herein, the term "cultivation" means that the microorganism is grown under appropriately controlled environmental conditions. The cultivation process of the present disclosure can be performed in a suitable culture medium and culture conditions known in the art. Such a cultivation process may be easily adjusted for use by those skilled in the art according to the strain to be selected. Specifically, the cultivation process may be performed in batch culture, continuous culture, and fed-batch culture known in the art, but the cultivation process is not limited thereto.

As used herein, the term "medium" refers to a mixture of materials which contains nutrient materials required for the cultivation of the microorganism as an main ingredient, and it supplies nutrient materials, growth factors, etc. along with water that is essential for survival and growth. Specifically, the medium and other culture conditions used for culturing the microorganism of the present disclosure may be any medium used for conventional cultivation of microorganisms without any particular limitation. However, the microorganism of the present disclosure may be cultured under aerobic conditions in a conventional medium containing an appropriate carbon source, nitrogen source, phosphorus source, inorganic compound, amino acid, and/or vitamin, etc. while adjusting temperature, pH, etc.

In the present disclosure, the carbon source may include carbohydrates (e.g., glucose, fructose, sucrose, maltose, etc.); sugar alcohols (e.g., mannitol, sorbitol, etc.); organic acid (e.g., pyruvic acid, lactic acid, citric acid, etc.); amino acids (e.g., glutamic acid, methionine, lysine, etc.), etc. Additionally, the carbon source may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but the carbon sources are not limited thereto.

Examples of the nitrogen source may include inorganic nitrogen sources (e.g., ammonia, ammonium sulfate, ammonium chloride, ammonium acetate, ammonium phosphate, ammonium carbonate, ammonium nitrate, etc.); amino acids (glutamic acid, methionine, glutamine, etc.); and organic nitrogen sources (e.g., peptone, N—Z amine, meat extract, yeast extract, malt extract, corn steep liquor, casein hydrolysate, fish or decomposition product thereof, defatted soybean cake or decomposition product thereof, etc.). These nitrogen sources may be used alone or in a combination of two or more kinds, but the nitrogen sources are not limited thereto.

Examples of the phosphorus source may include monopotassium phosphate, dipotassium phosphate, corresponding sodium-containing salts, etc. Examples of the inorganic compound may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch culture or continuous culture, but are not limited thereto.

In the present disclosure, the pH of a medium may be adjusted during the cultivation of a microorganism by adding a compound such as ammonium hydroxide, potassium hydroxide, ammonia, phosphoric acid, sulfuric acid, etc. to the medium in an appropriate manner. Additionally, during the cultivation, an antifoaming agent (e.g., fatty acid polyglycol ester) may be added to prevent foam generation. Additionally, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium, but the gas is not limited thereto.

The medium temperature may be in a range from 20° C. to 50° C., and specifically, from 30° C. to 37° C., but the temperature is not limited thereto. The cultivation may be continued until the useful materials are obtained in desired amounts, and specifically for 10 to 100 hours, but the cultivation is not limited thereto.

In the step of recovering tryptophan, the desired tryptophan may be recovered from the medium using the method of culturing a microorganism of the present disclosure, for example, using a suitable method known in the art according to a batch culture process, continuous culture process, or fed-batch culture process. For example, methods such as centrifugation, filtration, treatment with a protein crystallizing precipitant (salting-out method), extraction, ultrasonic disruption, ultrafiltration, dialysis, various kinds of chromatographies (e.g., molecular sieve chromatography (gel filtration), adsorption chromatography, ion exchange chromatography, affinity chromatography, etc.), and HPLC may be used alone or in combination, but the methods are not limited thereto.

The step of recovering may further include a purification process. The recovered L-tryptophan can be purified using an appropriate purification method known in the art.

Still another aspect of the present disclosure provides a method for increasing an L-tryptophan-exporting activity of a microorganism, which comprises introducing a protein having an L-tryptophan-exporting activity comprising the amino acid sequence of SEQ ID NO: 1 into a microorganism or enhancing the activity thereof.

Still another aspect of the present disclosure provides a use of a protein having an L-tryptophan-exporting activity comprising the amino acid sequence of SEQ ID NO: 1, for increasing the L-tryptophan-exporting activity in a microorganism.

The protein having an L-tryptophan-exporting activity comprising the amino acid sequence of SEQ ID NO: 1, introduction of the protein, and enhancement of the protein activity are as described above.

Advantageous Effects of the Invention

The inventors of the present disclosure have discovered a novel exporting gene having specificity to L-tryptophan and have attempted to express the gene in a microorganism producing L-tryptophan. As a result, they have confirmed that the microorganism can significantly improve the amount of L-tryptophan production compared to its parent strain, in which the gene is not expressed, thereby confirming that L-tryptophan can be effectively produced in the above microorganism.

BRIEF DESCRIPTION OF DRAWINGS

FIG. 1 shows the intracellular concentrations of tryptophan in CA04-8352 and CA04-8405, which are modified strains of *Corynebacterium glutamicum*, according to glucose consumption.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

Example 1: Screening and Selection of Exporting Genes

As a result of a PSI-BLAST screen based on NCBI and KEGG databases with the amino acid sequence of YdeD (i.e., an EamA family derived from *E. coli*) as a query sequence, 30 candidate genes, which are considered as membrane proteins capable of exporting tryptophan, and bioorganisms possessing these genes were selected. Among them, 5 kinds of bioorganisms were selected in consideration of biosafety levels, which are applicable to producing strains, and availability as shown in Table 1 below.

TABLE 1

Microorganisms expected to possess membrane protein capable of exporting aromatic amino acids

| No. | Strain | Protein Registration No. | Genome Registration No. | Biosafety Level |
|---|---|---|---|---|
| 1 | *Herbaspirillum rhizosphaerae* (KCTC12558) | WP_050478745.1 | NZ_LFLU01000012.1 | 1 |
| 2 | *Pseudomonas stutzeri* (KCTC22466) | WP_037022429.1 | NC_018177.1 | 1 |
| 3 | *Alcaligenes faecalis* (KCTC2678) | WP_045930186.1 | NZ_CP013119.1 | 1 |
| 4 | *Cupriavidus necator* (KCTC22469) | WP_011616478.1 | AM260480.1 | 1 |
| 5 | *Escherichia coli* str. K-12 substr. MG1655 | WP_000198205.1 | NC_000913.3 | 1 |

Example 2: Preparation of Microorganism of the Genus *Corynebacterium* where Gene Derived from *Herbaspirillum rhizosphaerae* is Introduced The gene encoding the membrane protein derived from *Herbaspirillum rhizosphaerae* selected in Example 1 has the amino acid sequence of SEQ ID NO: 1. The information on the gene encoding the membrane protein and adjacent nucleotide sequences thereof (Registration No. NZ_LFLU01000012.1) was obtained from NIH GenBank.

Primers to insert a gene derived from *Herbaspirillum rhizosphaerae* into the genomic DNA of *Corynebacterium glutamicum* were synthesized based on the obtained information of the nucleotide sequences. To amplify the gene derived from *Herbaspirillum rhizosphaerae*, PCR was performed using the chromosomal DNA of the *Herbaspirillum rhizosphaerae* strain as a template along with the primers of SEQ ID NO: 3 and SEQ ID NO: 4. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

As a result, a 956 bp gene fragment which comprises the 924 bp gene (SEQ ID NO: 2) was obtained.

```
(wex-1)
                                              SEQ ID NO: 3
TAGAGGAGACACAACATGAATAGCAAGAAGGCCAC (wex-2)
                                              SEQ ID NO: 4
ggctcttcctgtttAGTCTACAAACAGTCCGCCAC
```

To obtain the gapA promoter derived from *Corynebacterium glutamicum*, PCR was performed using the genomic DNA of *Corynebacterium glutamicum* as a template along with the primers of SEQ ID NO: 5 and SEQ ID NO: 6. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 30 seconds; and polymerization at 72° C. for 5 minutes.

```
(PgapA-1)
                                              SEQ ID NO: 5
cccttccggtttAGTTTGAAGCCAGTGTGAGTTGC (PgapA(-wex)-2)
                                              SEQ ID NO: 6
CTTCTTGCTATTCATGTTGTGTCTCCTCTAAAGATTGTA
```

The amplified gapA promoter region, the gene fragments derived from *Herbaspirillum rhizosphaerae*, and the pDZTn vector (KR Patent No. 10-1126041), which was cleaved with ScaI restriction enzyme, were cloned by the Gibson assembly method (DG Gibson et al., *NATURE METHODS*, VOL. 6 NO. 5, May 2009, NEBuilder HiFi DNA Assembly Master Mix), and thereby a recombinant plasmid was obtained. The recombinant plasmid was named as pDZTn-PgapA-Hrh. The cloning was performed by mixing the Gibson assembly reagent and each of the gene fragments in a calculated number of moles followed by incubating at 50° C. for 1 hour.

The prepared pDZTn-PgapA-Hrh vector was transformed into a wild-type *Corynebacterium glutamicum* ATCC13869 strain by electroporation (Appl. Microbiol. Biotechnol. (1999) 52:541 to 545) and subjected to a secondary crossover to obtain a strain in which one copy of the PgapA-Hrh gene is inserted into transposon on the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region of homologous recombination where the corresponding gene is inserted.

```
(Confirm_PgapA-wex-1)
                                              SEQ ID NO: 7
CGGATTATGCCAATGATGTG (Confirm_PgapA-wex-2)
                                              SEQ ID NO: 8
CACGATCACCAACATTCAGG
```

The thus-obtained strain was named as *Corynebacterium glutamicum* ATCC13869::PgapA-Hrh.

Example 3: Preparation of Microorganism of the Genus *Corynebacterium* where Gene Derived from *Pseudomonas stutzeri* is Introduced The gene encoding the membrane protein derived from *Pseudomonas stutzeri* selected in Example 1 has the amino acid sequence of SEQ ID NO: 9. The information on the corresponding gene and adjacent nucleotide sequences thereof (Registration No. NC_018177.1) was obtained from NIH GenBank.

Primers to insert a gene derived from *Pseudomonas stutzeri* into the genomic DNA of *Corynebacterium glutamicum* were synthesized based on the obtained information of the nucleotide sequences. To amplify the gene derived from *Pseudomonas stutzeri*, PCR was performed in the same manner as in Example 2 using the chromosomal DNA of the *Pseudomonas stutzeri* strain as a template along with the primers of SEQ ID NO: 11 and SEQ ID NO: 12.

As a result, a 977 bp gene fragment which comprises the 945 bp exporter gene (SEQ ID NO: 10) was obtained.

```
(Pst-1)
                                              SEQ ID NO: 11
TAGAGGAGACACAACATGAAAAACCAGCGTAAAGC (Pst-2)
                                              SEQ ID NO: 12
ggctcttcctgtttAGTTTATCCGTTTCGACGCGG
```

For the use of gapA promoter derived from *Corynebacterium glutamicum*, PCR was performed in the same manner as in Example 2 using the genomic DNA of *Corynebacterium glutamicum* ATCC13869 as a template along with the primers of SEQ ID NO: 5 and SEQ ID NO: 13.

```
(PgapA(-Pst)-2)
                                              SEQ ID NO: 13
ACGCTGGTTTTTCATGTTGTGTCTCCTCTAAAGATTGTA
```

The amplified gapA promoter region, the gene fragments derived from *Pseudomonas stutzeri*, and the pDZTn vector, which was cleaved with ScaI restriction enzyme, were cloned by the Gibson assembly method, and thereby a recombinant plasmid was obtained. The recombinant plasmid was named as pDZTn-PgapA-Pst. The cloning was performed by mixing the Gibson assembly reagent and each of the gene fragments in a calculated number of moles followed by incubating at 50° C. for 1 hour.

The prepared pDZTn-PgapA-Pst vector was transformed into a wild-type *Corynebacterium glutamicum* ATCC13869 strain by electroporation (Appl. Microbiol. Biotechnol. (1999) 52:541 to 545) and subjected to a secondary crossover to obtain a strain in which one copy of the PgapA-Pst gene is inserted into transposon on the chromosome. The corresponding genetic manipulation was confirmed through genome sequencing and PCR method using the primers of SEQ ID NO: 7 and SEQ ID NO: 8, each of which can respectively amplify the external region of the upstream region and downstream region of homologous recombination where the corresponding gene is inserted.

The thus-obtained strain was named as *Corynebacterium glutamicum* ATCC13869::PgapA-Pst.

Example 4: Preparation of Microorganism of the Genus *Corynebacterium* where Gene Derived from *Alcaligenes faecalis* is Introduced The gene encoding the membrane protein derived from *Alcaligenes faecalis* selected in Example 1 has the amino acid sequence of SEQ ID NO: 14. The information on the corresponding gene and adjacent nucleotide sequences thereof (Registration No. NZ_CP013119.1) was obtained from NIH GenBank.

Primers to insert a gene derived from *Alcaligenes faecalis* into the genomic DNA of *Corynebacterium glutamicum* were synthesized based on the obtained information of the nucleotide sequences. To amplify the gene derived from *Alcaligenes faecalis*, PCR was performed in the same manner as in Example 2 using the chromosomal DNA of the *Alcaligenes faecalis* strain as a template along with the primers of SEQ ID NO: 16 and SEQ ID NO: 17.

As a result, a 943 bp gene fragment which comprises the 912 bp exporter gene (SEQ ID NO: 15) was obtained.

```
(Afa-1)
                                         SEQ ID NO: 16
TAGAGGAGACACAACATGAAGCAATCTGATAAGGC (Afa-2)
                                         SEQ ID NO: 17
gctcttcctgtttAGTTCAGGCAGCGCTTTTTAGT
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 18.

```
(PgapA(-Afa)-2)
                                         SEQ ID NO: 18
ATCAGATTGCTTCATGTTGTGTCTCCTCTAAAGATTGTA
```

The amplified gapA promoter region, gene fragments derived from *Alcaligenes faecalis*, and the pDZTn vector, which was cleaved with ScaI restriction enzyme, were cloned by the Gibson assembly method, and thereby a recombinant plasmid was obtained. The recombinant plasmid was named as pDZTn-PgapA-Afa. The cloning was performed by mixing the Gibson assembly reagent and each of the gene fragments in a calculated number of moles followed by incubating at 50° C. for 1 hour.

The prepared pDZTn-PgapA-Afa vector was transformed into a wild-type *Corynebacterium glutamicum* ATCC13869 strain by electroporation and subjected to a secondary crossover to obtain a strain in which one copy of the PgapA-Afa gene is inserted into transposon on the chromosome. The corresponding genetic manipulation was confirmed through genome sequencing and PCR method using the primers of SEQ ID NO: 7 and SEQ ID NO: 8, each of which can respectively amplify the external region of the upstream region and downstream region of homologous recombination where the corresponding gene is inserted.

The thus-obtained strain was named as *Corynebacterium glutamicum* ATCC13869::PgapA-Afa.

Example 5: Preparation of Microorganism of the Genus *Corynebacterium* where Gene Derived from *Cupriavidus Necator* is Introduced The gene encoding the membrane protein derived from *Cupriavidus necator* selected in Example 1 has the amino acid sequence of SEQ ID NO: 19. The information on the corresponding gene and adjacent nucleotide sequences thereof (Registration No. AM260480.1) was obtained from NIH GenBank.

Primers to insert a gene derived from *Cupriavidus necator* into the genomic DNA of *Corynebacterium glutamicum* were synthesized based on the obtained information of the nucleotide sequences. To amplify the gene derived from *Cupriavidus necator*, PCR was performed in the same manner as in Example 2 using the chromosomal DNA of the *Cupriavidus necator* strain as a template along with the primers of SEQ ID NO: 21 and SEQ ID NO: 22.

As a result, a 977 bp gene fragment which comprises the 945 bp exporter gene derived from *Cupriavidus necator* (SEQ ID NO: 20) was obtained.

```
(Cne-1)
                                         SEQ ID NO: 21
TAGAGGAGACACAACATGCAAAGCAAGAGCAAAGC (Cne-2)
                                         SEQ ID NO: 22
ggctcttcctgtttAGTTCACGGTTCCTGGACACG
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 23.

```
(PgapA(-Cne)-2)
                                         SEQ ID NO: 23
GCTCTTGCTTTGCATGTTGTGTCTCCTCTAAAGATTGTA
```

The amplified gapA promoter region, gene fragments derived from *Cupriavidus necator*, and the pDZTn vector, which was cleaved with ScaI restriction enzyme, were cloned by the Gibson assembly method, and thereby a recombinant plasmid was obtained. The recombinant plasmid was named as pDZTn-PgapA-Cne. The cloning was performed by mixing the Gibson assembly reagent and each of the gene fragments in a calculated number of moles followed by incubating at 50° C. for 1 hour.

The prepared pDZTn-PgapA-Cne vector was transformed into a wild-type *Corynebacterium glutamicum* ATCC13869 strain by electroporation and subjected to a secondary crossover to obtain a strain in which one copy of the PgapA-Cne gene is inserted between transposon genes on the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region of homologous recombination where the corresponding gene is inserted.

The thus-obtained strain was named as *Corynebacterium glutamicum* ATCC13869::PgapA-Cne.

Example 6: Preparation of Microorganism of the Genus *Corynebacterium* where Gene Derived from *Escherichia coli* Str. K-12 Substr. MG1655 is Introduced The gene encoding the membrane protein derived from *Escherichia coli* str. K-12 substr. MG1655 selected in Example 1 has the amino acid sequence of SEQ ID NO: 24. The information on the corresponding gene and adjacent nucleotide sequences thereof (Registration No. NC_000913.3) was obtained from NIH GenBank.

Primers to insert a gene derived from *Escherichia coli* into the genomic DNA of *Corynebacterium glutamicum* were synthesized based on the obtained information of the nucleotide sequences. To amplify the gene derived from *Escherichia coli*, PCR was performed in the same manner as in Example 2 using the chromosomal DNA of the *Escherichia coli* strain as a template along with the primers of SEQ ID NO: 26 and SEQ ID NO: 27.

As a result, a 913 bp gene fragment which comprises the 882 bp exporter gene (SEQ ID NO: 25) was obtained.

```
(Eco-1)
                                        SEQ ID NO: 26
TAGAGGAGACACAACATGACACGACAAAAAGCAAC (Eco-2)
                                        SEQ ID NO: 27
gctcttcctgtttAGTTTAACCACGACGTGTCGCC
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 28.

```
(PgapA(-Eco)-2)
                                        SEQ ID NO: 28
TTTTTGTCGTGTCATGTTGTGTCTCCTCTAAAGATTG
```

The amplified gapA promoter region, gene fragments derived from *Escherichia coli*, and the pDZTn vector, which was cleaved with ScaI restriction enzyme, were cloned by the Gibson assembly method, and thereby a recombinant plasmid was obtained. The recombinant plasmid was named as pDZTn-PgapA-Eco. The cloning was performed by mixing the Gibson assembly reagent and each of the gene fragments in a calculated number of moles followed by incubating at 50° C. for 1 hour.

The prepared pDZTn-PgapA-Eco vector was transformed into a wild-type *Corynebacterium glutamicum* ATCC13869 strain by electroporation and subjected to a secondary crossover to obtain a strain in which one copy of the PgapA-Eco gene is inserted between transposon genes on the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region of homologous recombination where the corresponding gene is inserted.

The thus-obtained strain was named as *Corynebacterium glutamicum* ATCC13869::PgapA-Eco.

Example 7: Measurement of MICs in Microorganism Strains of the Genus *Corynebacterium* where Gene Derived from Various Microorganisms are Introduced To confirm the presence of tryptophan-exporting activity in the 5 types of *Corynebacterium glutamicum* strains prepared in Examples 2 to 6 (i.e., ATCC13869::PgapA-Hrh, ATCC13869::PgapA-Pst, ATCC13869::PgapA-Afa, ATCC13869::PgapA-Cne, and ATCC13869::PgapA-Eco), the minimum inhibitory concentration (MIC) experiment was performed using a tryptophan analogue and an analogue of phenylalanine (i.e., another aromatic amino acid). The 5 different strains of *Corynebacterium glutamicum*, each introduced with a gene encoding a membrane protein, were cultured in the minimal liquid medium at 30° C. for 24 hours, diluted to a concentration of $3 \times 10^3$ cells and $3 \times 10^4$ cells, respectively, and then spotting-cultured in minimal solid medium where a tryptophan analogue and a phenylalanine analogue is added.

For the minimum inhibitory concentration (MIC) experiment, p-fluoro-DL-phenylalanine (2.5 mg/mL) or 5-fluoro-DL-tryptophan (0.25 μg/mL) was added to the minimal solid medium, and the cell growth was observed after 60 hours (Table 2).

All of the introductions of the selected 5 types of genes enabled cell growth under a condition where the phenylalanine analogue was added at a concentration of 2.5 mg/mL. Among them, the introduction of genes derived from *Herbaspirillum rhizosphaerae*, *Alcaligenes faecalis*, and *Escherichia coli* showed the highest cell growth. The introduction of the gene derived from *Pseudomonas stutzeri* showed slightly reduced cell growth and the introduction of the gene derived from *Cupriavidus necator* showed the lowest cell growth. Under the same condition, the wild-type ATCC13869 strain did not grow. Additionally, under the condition where the tryptophan analogue was added at a concentration of 0.25 μg/mL, only the introduction of the gene derived from *Herbaspirillum rhizosphaerae* enabled cell growth.

From the above results, it was observed that all of the introductions of the selected 5 types of genes showed resistance to phenylalanine and the phenylalanine analogue even though there were differences in activities among the introductions. In contrast, with regard to tryptophan and the tryptophan analogue, only the introduction of the gene derived from *Herbaspirillum* rhizosphaera showed specific and excellent resistance thereto. Based on these results, it can be interpreted that only the membrane protein encoded by the gene derived from *Herbaspirillum* rhizosphaera can act as an exporter protein for tryptophan.

Minimal Medium (pH 7.2)

Glucose 10 g, $KH_2PO_4$ 1 g, $K_2HPO_4$ 2 g, $MgSO_4$ $7H_2O$ 0.4 g, Urea 2 g, $(NH_4)_2SO_4$ 5 g, NaCl 0.5 g, Nicotinamide 5 μg, Calcium pantothenate 0.1 μg, Biotin 0.2 μg, Thiamine HCl 3 μg, Trace elements solution 1 mL (based on 1 L of distilled water)

Trace Elements Solution $Na_2B_4O_7$ $10H_2O$ 0.09 g, $(NH_4)_6Mo_7O_{27}$ $4H_2O$ 0.04 g, $ZnSO_4$ $7H_2O$ 0.01 g, $CuSO_4$ $5H_2O$ 0.27 g, $MnCl_2$ $4H_2O$ 0.01 g, $FeCl_3$ $6H_2O$ 1 g, $CaCl_2$ 0.01 g (based on 1 L of distilled water)

TABLE 2

Growth of *Corynebacterium glutamicum* strains, in which genes derived from various microorganisms are introduced, in minimal medium containing a phenylalanine analogue or tryptophan analogue

| | Growth | |
|---|---|---|
| Strain | p-Fluoro phenylalanine (2.5 mg/mL) | 5'-Fluoro tryptophan (0.25 µg/mL) |
| ATCC13869 | − | − |
| ATCC13869::PgapA-Hrh | ++ | +++ |
| ATCC13869::PgapA-Pst | ++ | − |
| ATCC13869::PgapA-Afa | +++ | − |
| ATCC13869::PgapA-Cne | + | − |
| ATCC13869::PgapA-Eco | +++ | − |

Example 8: Preparation of Expression Vector for *Escherichia coli* in which Genes Derived from Various Microorganisms are Introduced To confirm the resistance of the genes derived from various microorganisms selected in Example 1 to tryptophan or an analogue thereof in *Escherichia coli*, each of the genes was cloned into pCL1920 (i.e., an *E. coli* expression vector) and expressed with the yccA promoter of *E. coli* W3110.

To obtain a fragment of the gene derived from *Herbaspirillum rhizosphaerae*, PCR was performed using the chromosomal DNA of the *Herbaspirillum rhizosphaerae* strain as a template along with the primers of SEQ ID NO: 29 and SEQ ID NO: 30. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

```
(Hrh-3)
                                   SEQ ID NO: 29
ATAGAGAGTGACTCAATGAATAGCAAGAAGGCCAC (Hrh-4)
                                   SEQ ID NO: 30
TCGAGCTCGGTACCCCTACAAACAGTCCGCCAC
```

To obtain the yccA promoter derived from *E. coli* W3110, PCR was performed using the genomic DNA of the *E. coli* W3110 as a template along with the primers of SEQ ID NO: 31 and SEQ ID NO: 32. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 10 seconds; and polymerization at 72° C. for 5 minutes.

```
(PyccA-1)
                                   SEQ ID NO: 31
CTCTAGAGGATCCCCTTCCAGATCAAATGCGTAA (PyccA(-Hrh)-2)
                                   SEQ ID NO: 32
CTTCTTGCTATTCATTGAGTCACTCTCTATGACAG
```

The amplified yccA promoter region, gene fragments derived from *Herbaspirillum rhizosphaerae*, and the pCL1920 vector (pSC101 ori, Sp$^r$), which was cleaved with SmaI restriction enzyme, were cloned by the Gibson assembly method, and thereby a recombinant plasmid was obtained. The recombinant plasmid was named as pCL1920-PyccA-Hrh. The cloning was performed by mixing the Gibson assembly reagent and each of the gene fragments in a calculated number of moles followed by incubating at 50° C. for 1 hour. The obtained pCL1920-PyccA-Hrh was introduced into the wild-type *E. coli* W3110, and thereby W3110/pCL1920-PyccA-Hrh (i.e., a transformant where the gene is expressed) was prepared.

To obtain a fragment of the gene derived from *Pseudomonas stutzeri*, PCR was performed using the chromosomal DNA of the *Pseudomonas stutzeri* strain as a template along with the primers of SEQ ID NO: 33 and SEQ ID NO: 34. Additionally, PCR was performed in the same manner as in obtaining the gene fragment from *Herbaspirillum rhizosphaerae* strain described above except that the primer of SEQ ID NO: 35, which was used to obtain the yccA promoter derived from *E. coli* W3110 for use, was used.

```
(Pst-3)
                                   SEQ ID NO: 33
ATAGAGAGTGACTCAATGAAAAACCAGCGTAAAGC (Pst-4)
                                   SEQ ID NO: 34
TCGAGCTCGGTACCCTTATCCGTTTCGACGCGG (PyccA(-Pst)-2)
                                   SEQ ID NO: 35
ACGCTGGTTTTTCATTGAGTCACTCTCTATGACAG
```

As such, the recombinant plasmid was obtained and it was named as pCL1920-PyccA-Pst. The expression vector pCL1920-PyccA-Pst was transformed into wild-type *E. coli* W3110, and thereby W3110/pCL1920-PyccA-Pst (i.e., a transformant where the gene is expressed) was prepared.

The process of preparing a transformant, where the gene derived from *Alcaligenes faecalis* strain is expressed, was the same as described above except that PCR was performed using the chromosomal DNA of *Alcaligenes faecalis* as a template along with the primers of SEQ ID NO: 36 and SEQ ID NO: 37, and the primer of SEQ ID NO: 38 for obtaining the yccA promoter were used.

```
(Afa-3)
                                   SEQ ID NO: 36
ATAGAGAGTGACTCAATGAAGCAATCTGATAAGGC (Afa-4)
                                   SEQ ID NO: 37
TCGAGCTCGGTACCCTCAGGCAGCGCTTTTTAGT (PyccA(-Afa)-2)
                                   SEQ ID NO: 38
ATCAGATTGCTTCATTGAGTCACTCTCTATGACAG
```

As such, a recombinant plasmid into which the gene derived from *Alcaligenes faecalis* is cloned was obtained and named as pCL1920-PyccA-Afa. The expression vector pCL1920-PyccA-Afa was transformed into the wild-type *E. coli* W3110, and thereby W3110/pCL1920-PyccA-Afa (i.e., a transformant) was prepared.

To obtain a fragment of the gene derived from *Cupriavidus necator* strain, PCR was performed using the chromosomal DNA of the *Cupriavidus necator* strain as a template along with the primers of SEQ ID NO: 39 and SEQ ID NO: 40. Additionally, PCR was performed in the same manner as in obtaining the gene fragment from *Herbaspirillum rhizosphaerae* strain described above except that the primer of SEQ ID NO: 41, which was used to obtain the yccA promoter derived from *E. coli* W3110 for use, was used.

(Cne-3)
SEQ ID NO: 39
ATAGAGAGTGACTCAATGCAAAGCAAGAGCAAAGC (Cne-4)
SEQ ID NO: 40
TCGAGCTCGGTACCCTCACGGTTCCTGGACACG (PyccA(-Cne)-2)
SEQ ID NO: 41
GCTCTTGCTTTGCATTGAGTCACTCTCTATGACAG As such, a recombinant plasmid was obtained and named as pCL1920-PyccA-Cne. The expression vector pCL1920-PyccA-Cne was transformed into the wild-type *E. coli* W3110, and thereby W3110/pCL1920-PyccA-Cne (i.e., a transformant where the gene is expressed) was prepared.

To obtain a fragment of the gene derived from *Escherichia coli* strain, PCR was performed using the chromosomal DNA of the *Escherichia coli* str. K-12 substr. MG1655 strain as a template along with the primers of SEQ ID NO: 42 and SEQ ID NO: 43. Additionally, PCR was performed in the same manner as in obtaining the gene fragment from *Herbaspirillum rhizosphaerae* strain described above except that the primer of SEQ ID NO: 44, which was used to obtain the yccA promoter derived from *E. coli* W3110 for use, was used.

(Eco-3)
SEQ ID NO: 42
ATAGAGAGTGACTCAATGACACGACAAAAAGCAAC (Eco-4)
SEQ ID NO: 43
TCGAGCTCGGTACCCTTAACCACGACGTGTCGCC (PyccA(-Eco)-2)
SEQ ID NO: 44
TTTTTGTCGTGTCATTGAGTCACTCTCTATGACAG As such, a recombinant plasmid was obtained and named as pCL1920-PyccA-Eco. The expression vector pCL1920-PyccA-Eco was introduced into the wild-type *E. coli* W3110, and thereby W3110/pCL1920-PyccA-Cne (i.e., a transformant where the gene is expressed) was prepared.

Example 9: Measurement of MIC of *E. coli* in which Genes for Membrane Proteins Derived from Various Microorganisms are Overexpressed To confirm the resistance of *E. coli* strains where the 5 types of genes prepared in Example 8 are overexpressed (i.e., W3110/pCL1920-PyccA-Hrh, W3110/pCL1920-PyccA-Pst, W3110/pCL1920-PyccA-Afa, W3110/pCL1920-PyccA-Cne, and W3110/pCL1920-PyccA-Eco), the minimum inhibitory concentration (MIC) experiment was performed using a tryptophan analogue and a phenylalanine analogue. The *E. coli* strains where the 5 types of genes are overexpressed were cultured in M9 minimal liquid medium containing spectinomycin (50 µg/mL) at 37° C. for 15 hours, diluted at concentrations of $10^4$ cells and $10^5$ cells, respectively, and then spotting-cultured in M9 glucose minimal solid medium containing spectinomycin (50 µg/mL) where a tryptophan analogue or a phenylalanine analogue was added. For the minimum inhibitory concentration (MIC) experiment, p-fluoro-DL-phenylalanine (2 mg/mL) or 5-fluoro-DL-tryptophan (0.7 µg/mL) was added to the M9 minimal solid medium, and the cell growth was observed after 48 hours (Table 3).

*E. coli* strains showed excellent growth under the condition where the phenylalanine analogue was added when the genes derived from *E. coli* were overexpressed, and the overexpression of the gene derived from *Alcaligenes faecalis* also showed significant growth. However, the overexpression of the genes derived from *Herbaspirillum rhizosphaerae*, *Pseudomonas stutzeri*, and *Cupriavidus necator* failed to show comparable growth as in W3110/pCL1920 (i.e., the control group). In contrast, the overexpression of all of the 5 types of selected genes made it possible to grow all of the cells under the condition where the tryptophan analogue was added. Among them, the overexpression of the gene derived from *Herbaspirillum rhizosphaerae* showed the highest growth, and the overexpression of the exporter genes derived from *Alcaligenes faecalis* and *E. coli* showed the second highest growth. The overexpression of the exporter genes derived from *Pseudomonas stutzeri* and *Cupriavidus necator* showed negligible growth.

The results of the MIC experiment about the 5 types of genes in *E. coli* strain were similar to that in *C. glutamincum*. The gene derived from *Herbaspirillum rhizosphaerae* showed specific and excellent resistance to tryptophan and its analogue in both *Corynebacterium glutamicum* and *E. coli* strains, and the exporter gene derived from *E. coli* showed higher resistance of exportation to phenylalanine and its analogue than to tryptophan. From these results, it was suggested that the gene derived from *Herbaspirillum rhizosphaerae* shows a specific and excellent exporting ability for tryptophan in both *Corynebacterium glutamicum* and *E. coli* strains.

TABLE 3

Growth of *E. coli* strains where each gene is overexpressed in a minimal medium containing a phenylalanine analogue or a tryptophan analogue

| | Growth | |
| --- | --- | --- |
| Strain | p-Fluorophenylalanine (2.5 mg/mL) | 5'-Fluoro tryptophan (0.7 µg/mL) |
| W3110/pCL 1920 | − | − |
| W3110/pCL 1920-Py ccA-Hrh | − | ++++ |
| W3110/pCL 1920-Py ccA-Pst | − | + |
| W3110/pCL 1920-Py ccA-Afa | ++ | ++ |
| W3110/pCL 1920-Py ccA-Cne | − | + |
| W3110/pCL 1920-Py ccA-Eco | +++ | ++ |

Reference Example 1: Preparation of Microorganism of the Genus *Corynebacterium glutamicum* Producing L-Tryptophan The L-tryptophan-producing strains were developed from wild-type *Corynebacterium glutamicum* ATCC13869. Since the wild-type *Corynebacterium glutamicum* cannot produce L-tryptophan, or if possible, can produce only a very small amount, an attempt was made to use the strain where the biosynthesis pathway essential for the production of L-tryptophan was enhanced as the parent strain. Specifically, the expression of the operon of L-tryptophan biosynthetic genes were increased by enhancing the promoter. Additionally, to release the feedback inhibition of the TrpE protein, the 38th amino acid of trpE (i.e., serine) was substituted with arginine (*Journal of Bacteriology*, November 1987, p. 5330 to 5332).

For the above genetic manipulation, first, the upstream region of the trpE promoter and the downstream region of the 38th amino acid mutation of trpE were obtained for homologous recombination on the chromosome. Specifically, the genetic fragment of the upstream region of the trpE promoter was obtained by performing PCR using the chromosomal DNA of *Corynebacterium glutamicum* as a template along with the primers of SEQ ID NO: 45 and SEQ ID NO: 46, whereas the genetic fragment of the downstream region of the 38th amino acid mutation of trpE was obtained by performing PCR using the chromosomal DNA of *Corynebacterium glutamicum* as a template along with the primers of SEQ ID NO: 47 and SEQ ID NO: 48.

```
(Pspl7-trpE(S38R)_L-1)
                                        SEQ ID NO: 45
TCGAGCTCGGTACCCAAACAACTGCGACGTGTGTC (Pspl7-trpE(S38R)_L-2)
                                        SEQ ID NO: 46
CATGAAGCGCCGGTACCTTAATCATTTTTGGGTTC (Pspl7-trpE(S38R)_R-1)
                                        SEQ ID NO: 47
GCCCTGTTGGAACGCGCTGATATCACCACCAAGAA (Pspl7-trpE(S38R)_R-2)
                                        SEQ ID NO: 48
CTCTAGAGGATCCCCAGATGTCACCGTTGTAAATG
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 60 seconds; and polymerization at 72° C. for 5 minutes.

The PCR was performed using the synthesized promoter SPL7 (SEQ ID NO: 49) as a template along with the primers of SEQ ID NO: 50 and SEQ ID NO: 51.

```
(Pspl7-1)
                                        SEQ ID NO: 50
CCCAAAAATGATTAAGGTACCGGCGCTTCATGTCA (Pspl7-2)
                                        SEQ ID NO: 51
GGGATTCGTGCTCATGATATCTGTTTTGATCTCCTCC
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 30 seconds; and polymerization at 72° C. for 5 minutes.

To obtain the fragment of front sequences of trpE, including from 1st to the 38th amino acid mutation, derived from *Corynebacterium glutamicum*, PCR was performed using the genomic DNA of *Corynebacterium glutamicum* as a template along with the primers of SEQ ID NO: 52 and SEQ ID NO: 53.

```
(trpE (S38R)-1)
                                        SEQ ID NO: 52
ATCAAAACAGATATCATGAGCACGAATCCCCATGT (trpE (S38R)-2)
                                        SEQ ID NO: 53
GTGGTGATATCAGCGCGTTCCAACAGGGCTGCATC
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 30 seconds; and polymerization at 72° C. for 5 minutes.

A recombinant plasmid was obtained by cloning the amplified upstream region of the trpE promoter and the downstream region of the 38th amino acid mutation of trpE, the SPL7 promoter and the fragment of front sequence of trpE, and the pDZ vector which is cleaved by SmaI restriction enzyme using the Gibson assembly method. The recombinant plasmid was named as pDZ-PSPL7-trpE (S38R). The cloning was performed by mixing the Gibson assembly reagent and each of the gene fragments in a calculated number of moles followed by incubating at 50° C. for 1 hour.

The prepared pDZ-PSPL7-trpE (S38R) vector was transformed into the *Corynebacterium glutamicum* ATCC13869 strain by electroporation and subjected to a secondary crossover. Then a strain which a promoter of the trpE is replaced with SPL7 promoter (i.e., a stronger promoter) and the 38th amino acid of trpE (i.e., serine) is substituted with arginine on the chromosome, was obtained. The corresponding genetic manipulation was confirmed through genome sequencing and a PCR method using the primers of SEQ ID NO: 54 and SEQ ID NO: 55, which can amplify the upstream region and downstream region of homologous recombination where the gene is inserted, and the resulting strain was named as CA04-8325.

```
(Confirm_Pspl7-trpE(S38R)-1)
                                        SEQ ID NO: 54
GAAGAAGAGGCTGCAGATG (Confirm_Pspl7-trpE(S38R)-2)
                                        SEQ ID NO: 55
GATCAGCGCCATCATGTT
```

Tryptophan production occurs via the aromatic amino acid metabolic pathway, and this metabolic pathway starts from the condensation reaction between phosphoenolpyruvate and erythrose 4-phosphate. Accordingly, a smooth supply of these two precursors is essential for the production of tryptophan, and the overexpression of the tkt gene was performed for the smooth supply of erythrose 4-phosphate, which is known to be relatively deficient.

For the above genetic manipulation, PCR was performed using the chromosomal DNA of *Corynebacterium glutamicum* as a template along with the primers of SEQ ID NO: 56 and SEQ ID NO: 57 to obtain the upstream region for the additional insertion of the tkt gene, and along with the primers of SEQ ID NO: 58 and SEQ ID NO: 59 to obtain the downstream region for the additional insertion of the tkt gene.

```
(Pn-tkt_L-1)
                                        SEQ ID NO: 56
TCGAGCTCGGTACCCAAACTTTGAGTGGGTGCGTG (Pn-tkt_L-2)
                                        SEQ ID NO: 57
TCGAGCTACGAGGGCGGTTCCCAGCCCTTCATTAG (Pn-tkt_R-1)
                                        SEQ ID NO: 58
ATTAACGGTTAATTGATTCTGGACGTCATGACTAC (Pn-tkt_R-2)
                                        SEQ ID NO: 59
CTCTAGAGGATCCCCGCCTCGATGATGCAGTCGTC
```

Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 30 seconds; and polymerization at 72° C. for 5 minutes.

To obtain the tkt gene and its promoter, PCR was performed using the chromosomal DNA of wild-type *Corynebacterium glutamicum* ATCC13869 as a template along with the primers of SEQ ID NO: 60 and SEQ ID NO: 61, and thereby the tkt gene comprising its promoter was obtained.

```
(Pn-tkt-1)
                                          SEQ ID NO: 60
GAAGGGCTGGGAACCGCCCTCGTAGCTCGAGAGTT (Pn-tkt-2)
                                          SEQ ID NO: 61
CATGACGTCCAGAATCAATTAACCGTTAATGGAGTCC
```

Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute and 20 seconds; and polymerization at 72° C. for 5 minutes.

A recombinant plasmid was obtained by cloning the amplified upstream region for the additional insertion of the tkt gene and downstream region for the additional insertion of the tkt gene, the tkt gene comprising tkt promoter, and the pDZ vector for chromosomal transformation, which is cleaved by SmaI restriction enzyme using the Gibson assembly method, and the resultant recombinant plasmid was named as pDZ-Pn-tkt. The cloning was performed by mixing the Gibson assembly reagent and each of the gene fragments in a calculated number of moles followed by incubating at 50° C. for 1 hour.

The prepared pDZ-Pn-tkt vector was transformed into the CJ04-8325 strain by electroporation and subjected to a secondary crossover to obtain a strain in which the tkt gene comprising tkt promoter is inserted on the chromosome. The corresponding genetic manipulation was confirmed through genome sequencing and a PCR method using the primers of SEQ ID NO: 62 and SEQ ID NO: 63, which can respectively amplify the external region of the upstream region and downstream region of homologous recombination where the corresponding gene is inserted. The resulting strain was named as CA04-8352.

```
(Confirm_Pn-tkt-1)
                                          SEQ ID NO: 62
ACCCAGAACCCCAAATTTTC (Confirm_Pn-tkt-2)
                                          SEQ ID NO: 63
TTGAGTTCGACAACTTTGG
```

Example 10: Tryptophan Production by Microorganism of the Genus *Corynebacterium* where Genes Derived from *Herbaspirillum rhizosphaerae* and *E. coli* are Introduced The gene derived from *Herbaspirillum rhizosphaerae*, which showed excellent activity in the minimum inhibitory concentration of the tryptophan analogue in Example 7, was introduced into CA04-8352, which is a tryptophan-producing strain prepared in Reference Example 1. For this purpose, the pDZTn-PgapA-Hrh vector for the introduction of the gene derived from *Herbaspirillum rhizosphaerae* prepared in Example 2 was transformed into CA04-8352 (i.e., a tryptophan-producing strain) by electroporation and subjected to the process as in Example 2, and thereby a strain was obtained in which one copy of the gene derived from *Herbaspirillum rhizosphaerae* is inserted between transposon genes. The resulting strain was named as CA04-8405.

Additionally, the gene derived from *E. coli* was introduced into the CA04-8352 (i.e., a tryptophan-producing strain) as the control group. The pDZTn-PgapA-Eco vector for the introduction of the gene derived from *E. coli* prepared in Example 6 was transformed into CA04-8352 (i.e., a tryptophan-producing strain) by electroporation and subjected to the process as in Example 6, and thereby a strain was obtained in which one copy of the gene derived from *E. coli* is inserted between transposon genes. The resulting strain was named as CA04-8406.

The strains CA04-8405 and CA04-8406 obtained by the processes described above were cultured by the following method so as to confirm the amount of tryptophan production relative to the CA04-8352 strain prepared in Reference Example 1 as the control group. Each strain was inoculated into a 250 mL corner-baffle flask containing seed medium (25 mL) and cultured with shaking at 30° C. at 200 rpm for 20 hours. Then, each seed culture solution (1 mL) was inoculated into a 250 mL corner-baffle flask containing production medium (25 mL) and cultured with shaking at 30° C. at 200 rpm for 24 hours. Upon completion of the cultivation, the amount of L-tryptophan production was measured by HPLC.

Seed Medium (pH 7.0)
glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 μg, thiamine HCl 1,000 μg, calcium pantothenate 2,000 μg, nicotinamide 2,000 μg (based on 1 L of distilled water)

Production Medium (pH 7.0)
glucose 30 g, $(NH_4)_2SO_4$ 15 g, $MgSO_4$ $7H_2O$ 1.2 g, $KH_2PO_4$ 1 g, yeast extract 5 g, biotin 900 μg, thiamine HCl 4,500 μg, calcium pantothenate 4,500 μg, $CaCO_3$ 30 g (based on 1 L of distilled water)

TABLE 4

Confirmation of amount of L-tryptophan production by CA04-8352 (a *Corynebacterium glutamicum* strain producing L-tryptophan), CA04-8405 (a strain where a gene derived from *Herbaspirillum rhizosphaerae* is inserted), and CA04-8406 (a strain where a gene derived from *E. coli* is inserted)

|  | $OD_{562}$ | Amount of Tryptophan Production (g/L) | Tryptophan Yield (*100 g/g, %) |
|---|---|---|---|
| CA04-8352 | 56.5 | 0.25 | 0.83 |
| CA04-8405 | 52.3 | 1.52 | 5.07 |
| CA04-8406 | 56.1 | 0.24 | 0.80 |

The results of the L-tryptophan production CA04-8352, CA04-8405, and CA04-8406 strains in the medium are shown in Table 4 above.

The CA04-8405 strain in which the gene derived from *Herbaspirillum rhizosphaerae* is introduced produced L-tryptophan at a final concentration of 1.52 g/L in flask cultivation, and this is an improvement of about 5-fold compared to that of the CA04-8352 strain, the control group. This indicates that the gene derived from *Herbaspirillum rhizosphaerae* significantly improves L-tryptophan production in a *Corynebacterium glutamicum* strain. In contrast, the CA04-8406 strain, in which an *E. coli*-derived gene was introduced, produced L-tryptophan at a concentration of 0.23 g/L, which is almost the same as the amount of L-tryptophan production by the CA04-8352 strain (i.e., the parent strain of the CA04-8406 strain). As confirmed in the minimum inhibitory concentration (MIC) experiment of the tryptophan analogue and the phenylalanine analogue confirmed in Examples 7 and 9, the gene derived from *E. coli* is considered to be an exporter gene that shows higher specificity to phenylalanine than to tryptophan.

The CA04-8405 strain was internationally deposited at the Korean Culture Center of Microorganisms (KCCM), an international depositary, on Aug. 21, 2017, under the provisions of the Budapest Treaty and assigned accession number KCCM12099P (CA04-8405).

Example 11: Analysis of Intracellular Tryptophan Metabolites in *Corynebacterium glutamicum* where a Gene Derived from *Herbaspirillum rhizosphaerae* is Introduced To explicitly confirm whether the intracellular tryptophan concentration decreased as the tryptophan-exporting ability of the CA04-8405 strain (i.e., a tryptophan-producing strain) improved, the intracellular tryptophan concentration was measured for the CA04-8405 strain and its parent strain (i.e., CA04-8352), using the extraction method using an organic solvent.

The method for analyzing the intracellular metabolites was performed according to the method described in the reference (Nakamura J et al., *Appl. Environ. Microbiol.* 73(14): 4491 to 4498, 2007).

First, with regard to the modified *Corynebacterium glutamicum* strains of CA04-8352 and CA04-8405, each strain was inoculated into a 250 mL corner-baffle flask containing seed medium (25 mL) and cultured with shaking at 30° C. at 200 rpm for 20 hours. Then, each seed culture solution (1 mL) was inoculated into a 250 mL corner-baffle flask containing production medium (25 mL) and cultured with shaking at 30° C. at 200 rpm. The intracellular tryptophan concentration was analyzed three times according to glucose consumption. The cultured cells in each step were separated from the culture liquid by rapid vacuum filtration (Durapore HV, 0.45 m; Millipore, Billerica, Mass., USA). The filter to which cells were adsorbed was washed twice with distilled water (10 mL) and soaked in methanol containing 5 µM morpholine ethanesulfonic acid and 5 µM methionine sulfone for 10 minutes. Chloroform (1.6 mL) and distilled water (0.644) were added to the cell extract (1.6 mL) obtained above and thoroughly mixed, and only the aqueous phase was applied to the spin column to remove protein impurities. The filtered extract was analyzed using the capillary electrophoresis mass spectrometry, and the results are shown in FIG. 1.

As shown in FIG. 1, it was confirmed that the CA04-8405 strain showed a decrease of the intracellular tryptophan concentration to a level of 33% to 41%, compared to that of its parent strain, CA04-8352. From this, it can be interpreted that as the tryptophan produced within the cells of a *Corynebacterium glutamicum* strain due to the expression of the gene derived from *Herbaspirillum rhizosphaerae* was smoothly exported extracellularly, the intracellular tryptophan concentration of the CA04-8405 strain decreased. From the above results, it was confirmed that the gene derived from *Herbaspirillum rhizosphaerae* is a gene encoding a membrane protein having an exporting ability specific to tryptophan.

Reference Example 2: Preparation of Microorganism of the Genus *Escherichia* Producing L-Tryptophan The microorganism of the genus *Escherichia* producing L-tryptophan was developed from the wild-type *E. coli* W3110. To confirm whether the amount of tryptophan production significantly increases as the protein having an L-tryptophan-exporting activity is modified to be expressed, the strain prepared to produce L-tryptophan was used as the parent strain. Specifically, the expression of the L-tryptophan biosynthesis genes (trpEDCBA), which are involved in the production of L-tryptophan from chorismate, is inhibited by TrpR. Accordingly, the trpR gene encoding the TrpR was removed. Additionally, to release the feedback inhibition of the TrpE polypeptide according to the improvement of L-tryptophan production, the $21^{st}$ amino acid from the N-terminus of TrpE (i.e., proline) was substituted with serine (*J. Biochem. Mol. Biol.* 32, 20 to 24 (1999)).

The Mtr membrane protein has the role of introducing extracellular L-tryptophan into a cell, and the TnaA protein has the role of separating the intracellular L-tryptophan and water molecules into indole, pyruvate, and ammonia ($NH_3$). Accordingly, the mtr and tnaA genes that inhibit L-tryptophan production and decompose the same were removed.

For the removal of these genes, the λ-red recombination method (One-step inactivation of chromosomal genes in *Escherichia coli* K-12 using PCR products, Datsenko K A, Wanner B L., *Proc Natl Acad Sci USA*. 2000 Jun. 6; 97(12): 6640 to 6645) was used. For the removal of the mtr gene, PCR was performed using the pKD4 vector as a template along with the primers of SEQ ID NO: 64 and SEQ ID NO: 65, and thereby a gene fragment (1,580 bp), in which a FRT-kanamycin-FRT cassette and a pair of 50 bp homologous nucleotides flanking the mtr gene, where chromosomal homologous recombination occurs therebetween, are bound, was obtained. The kanamycin antibiotic marker of the pKD4 vector was used for the confirmation of removal of a target gene and insertion of an antibiotic gene, and the FRT region has the role of removing the antibiotic marker after the removal of the target gene. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(Δmtr cassette-1)

SEQ ID NO: 64

TGCAATGCATAACAACGCAGTCGCACTATTTTTCACTGGAGAGAAGCCC

TGTGTAGGCTGGAGCTGCTTC (Δmtr cassette-2)

SEQ ID NO: 65

TGCAATGCATAACAACGCAGTCGCACTATTTTTCACTGGAGAGAAGCCC

TGTCCATATGAATATCCTCCT

The pKD46 vector which expresses lambda red recombinase (gam, bet, and exo genes) were transformed into the *E. coli* W3110 strain by electroporation, and each strain was spread on LB solid medium containing kanamycin (50 mg/L). The *E. coli* W3110 strain in which the transformation of the pKD46 vector was confirmed induced the expression of a recombinant enzyme by adding 10 mM L-arabinose when the $OD_{600}$ reached about 0.1. When the $OD_{600}$ reached about 0.6, the strains were prepared into competent cells, and the linear gene fragment obtained in the above process, in which a FRT-kanamycin-FRT cassette and a pair of 50 bp homologous nucleotides flanking the mtr gene are bound, was transformed by electroporation. For the colonies grown on LB solid medium containing kanamycin (25 mg/L), colony PCR was performed using the primers of SEQ ID NO: 66 and SEQ ID NO: 67, and the colonies where the 782 bp gene fragment is prepared were selected.

(Confirm_Cassette-1)
SEQ ID NO: 66
GGGCAGGATCTCCTGTCATC (Confirm_Δmtr-2)
SEQ ID NO: 67
AAATGTCGGATAAGGCACCG The strains in which the mtr gene was removed due to homologous recombination were prepared into competent cells so as to remove the kanamycin antibiotic marker and then transformed with the pCP20 vector by electroporation. The pCP20 vector expresses the FLP protein and thereby recognizes the FRT sites flanking the kanamycin antibiotic and binds thereto on the chromosome, thereby removing the antibiotic marker between the FRT sites. The pCP20 vector-transformed strain grown on LB solid medium containing ampicillin (100 mg/L) and chloramphenicol (25 mg/L) was cultured in LB liquid medium at 30° C. for 1 hour, further cultured at 42° C. for 15 hours, and spread on LB solid medium. The grown colonies were cultured in LB solid medium containing ampicillin (100 mg/L) and chloramphenicol (25 mg/L); LB solid medium containing kanamycin (12.5 mg/L); and LB solid medium containing no antibiotic. Only the colonies which grew in LB solid medium containing no antibiotic were selected. The removal of the mtr gene was finally confirmed by genome sequencing and the strain was named as CA04-9300.

Genetic manipulation was performed by the method described above so as to remove the tnaA gene. PCR was performed using the pKD4 vector as a template along with the primers of SEQ ID NO: 68 and SEQ ID NO: 69, and thereby a gene fragment (1,580 bp), in which an FRT-kanamycin-FRT cassette and a pair of 50 bp homologous nucleotides flanking the tnaA gene, where chromosomal homologous recombination occurs therebetween, are bound, was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(ΔtnaA cassette-1)
SEQ ID NO: 68
TGTAATATTCACAGGGATCACTGTAATTAAAATAAATGAAGGATTATGT

AGTGTAGGCTGGAGCTGCTTC (ΔtnaA cassette-2)
SEQ ID NO: 69
TGTAGGGTAAGAGAGTGGCTAACATCCTTATAGCCACTCTGTAGTATTA

AGTCCATATGAATATCCTCCT

The pKD46 plasmid was transformed into the CA04-9300. The CA04-9300, in which the recombinases were expressed by the addition of 10 mM L-arabinose was transformed by electroporation with the linear gene fragment obtained in the above process, in which an FRT-kanamycin-FRT cassette and a pair of 50 bp homologous nucleotides flanking the tnaA gene are bound. For the colonies grown on LB solid medium containing kanamycin (25 mg/L), colony PCR was performed using the primers of SEQ ID NO: 66 and SEQ ID NO: 70, and the colonies where the 787 bp gene fragment is prepared were selected.

(Confirm_ΔtnaA-2)
SEQ ID NO: 70
ACATCCTTATAGCCACTCTG

The strains in which the tnaA gene was removed due homologous recombination were prepared into competent cells so as to remove the kanamycin antibiotic marker and then transformed with the pCP20 vector, and a strain where the kanamycin antibiotic marker was removed by the expression of the FLP protein was prepared. The removal of the tnaA gene was finally confirmed by genome sequencing and the strain was named as CA04-9301.

To remove the trpR gene, PCR was performed using the pKD4 vector as a template along with the primers of SEQ ID NO: 71 and SEQ ID NO: 72, and thereby the gene fragment (1,580 bp), in which an FRT-kanamycin-FRT cassette and a pair of 50 bp homologous nucleotides flanking the trpR gene, where chromosomal homologous recombination occurs therebetween, are bound, was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(ΔtrpR cassette-1)
SEQ ID NO: 71
TACAACCGGGGGAGGCATTTTGCTTCCCCCGCTAACAATGGCGACATAT

TGTGTAGGCTGGAGCTGCTTC (ΔtrpR cassette-2)
SEQ ID NO: 72
GCATTCGGTGCACGATGCCTGATGCGCCACGTCTTATCAGGCCTACAAA

AGTCCATATGAATATCCTCCT

The pKD46 plasmid was transformed into the CA04-9301. The CA04-9301 in which the recombinases were expressed by the addition of 10 mM L-arabinose was transformed by electroporation with the linear gene fragment obtained in the above process, in which an FRT-kanamycin-FRT cassette and a pair of 50 bp homologous nucleotides flanking the trpR gene are bound. For the colonies grown on LB solid medium containing kanamycin (25 mg/L), colony PCR was performed using the primers of SEQ ID NO: 66 and SEQ ID NO: 73, and the colonies where the 838 bp gene fragment is prepared were selected.

(Confirm_ΔtrpR-2)
SEQ ID NO: 73
AGGACGGATAAGGCGTTCAC

The strains in which the trpR gene was removed due to homologous recombination were prepared into competent cells so as to remove the kanamycin antibiotic marker and then transformed with the pCP20 vector, and a strain where the kanamycin antibiotic marker was removed by the expression of the FLP protein was prepared. The removal of the trpR gene was finally confirmed by genome sequencing and the strain was named as CA04-9307.

To provide the CA04-9307 strain with the feedback resistant trpE trait, PCR was performed using the E. coli W3110 gDNA as a template along with the primers of SEQ ID NO: 74 and SEQ ID NO: 75, which contain an EcoRI restriction site, and thereby a trpE gene fragment containing an EcoRI restriction site (1,575 bp) was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 1 minute, and polymerization at 72° C. for 1 minute; and polymerization at 72° C. for 5 minutes.

```
(trpE-1)
                                        SEQ ID NO: 74
GAATTCATGCAAACACAAAAACCGAC (trpE-2)
                                        SEQ ID NO: 75
GAATTCTCAGAAAGTCTCCTGTGCA
```

Cloning was performed after treating the trpE gene fragment obtained by the above method and the pSG76-C plasmid (*Journal of Bacteriology*, July 1997, p. 4426 to 4428) with EcoRI restriction enzyme, respectively. The cloned plasmid was transformed into E. coli DH5a by electroporation, and the transformed E. coli DH5a strains were selected on LB plates containing chloramphenicol (25 μg/mL) and thereby the pSG76-C-trpE plasmid was obtained.

The pSG76-C-trpE(P21S) was prepared using the obtained pSG76-C-trpE plasmid along with the primers of SEQ ID NO: 76 and SEQ ID NO: 77 by site-directed mutagenesis (Stratagene, USA).

```
(trpE(P21S)-1)
                                        SEQ ID NO: 76
CGCTTATCGCGACAATTCCACCGCGCTTTTTCACCAG (trpE(P21S)-2)
                                        SEQ ID NO: 77
CTGGTGAAAAAGCGCGGTGGAATTGTCGCGATAAGCG
```

The pSG76-C-trpE(P21S) plasmid was transformed into the CA04-9307 strain, cultured in LB-Cm medium (yeast extract 10 g/L, NaCl 5 g/L, tryptone 10 g/L, and chloramphenicol 25 μg/L), and colonies having resistance to chloramphenicol were selected. The selected transformants are strains in which the pSG76-C-trpE(P21S) plasmid is incorporated into the trpE region of the genome by first insertion. The strain in which the obtained trpE(P21S) gene is inserted was transformed with the pAScep plasmid (*Journal of Bacteriology*, July 1997, p. 4426 to 4428), which expresses restriction enzyme I-SceI that cleaves the I-SceI region present in the pSG76-C plasmid, and the strain which grew in the LB-Ap (yeast extract 10 g/L, NaCl 5 g/L, tryptone 10 g/L, and ampicillin 100 μg/L) was selected. The trpE gene in the selected strain was amplified using the primers of SEQ ID NO: 74 and SEQ ID NO: 75, and it was confirmed that the amplified trpE gene was replaced with the trpE(P21S) gene by sequencing. The thus prepared strain was named as CA04-4303.

Example 12: L-Tryptophan Production by Microorganism of the Genus *Escherichia* in which a Gene Derived from *Herbaspirillum rhizosphaerae* is Introduced The pCL1920-PyccA-Hrh prepared in Example 8 was introduced into the CA04-4303 strain prepared in Reference Example 2, and thereby a CA04-4306 strain in which a gene derived from *Herbaspirillum rhizosphaerae* is overexpressed was prepared. Additionally, the pCL1920 vector, as a control group, was transformed into the CA04-4303 strain. To examine the amount of L-tryptophan production in the two strains (i.e., CA04-4303/pCL1920 and CA04-4306), these strains were cultured in LB liquid medium containing spectinomycin (50 mg/L) for 12 hours. Then, these strains were each inoculated into a 250 mL corner-baffle flask containing 25 mL of production medium such that the initial $OD_{600}$ value becomes 0.01 and then cultured with shaking at 37° C. at 200 rpm for 48 hours. Upon completion of the cultivation, the amount of L-tryptophan production was measured by HPLC.

The results with regard to the L-tryptophan production in CA04-4303/pCL1920 and CA04-4306 strains in medium are shown in Table 5 below. The strain CA04-4306, in which a gene derived from *Herbaspirillum rhizosphaerae* was introduced and overexpressed, showed a final L-tryptophan of 2.1 g/L in the flask cultivation, which is about 50% higher than that of the control group. This indicates that the gene derived from *Herbaspirillum rhizosphaerae* exports L-tryptophan even in E. coli, thereby significantly improving its L-tryptophan production.

Production Medium (pH 7.0)

Glucose 70 g, $(NH_4)_2SO_4$ 20 g, $MgSO_4$ $7H_2O$ 1 g, $KH_2PO_4$ 2 g, yeast extract 2.5 g, Na-citrate 5 g, NaCl 1 g, $CaCO_3$ 40 g (based on 1 L of distilled water)

TABLE 5

Confirmation of L-tryptophan production in E. coli-derived L-tryptophan-producing strain (CA04-4303) and the L-tryptophan-producing strain where the exporter gene derived from *Herbaspirillum rhizosphaerae* is overexpressed (CA04-4306)

| | $OD_{600}$ | Amount of Tryptophan Production (g/L) | Tryptophan Yield (*100 g/g, %) |
|---|---|---|---|
| CA04-4303/pCL1920 | 43.7 | 1.4 | 2 |
| CA04-4306 | 42 | 2.1 | 3 |

Accordingly, as can be seen in the results of Examples 7 and 9, the gene derived from *Herbaspirillum rhizosphaerae* showed high specificity and excellent resistance to L-tryptophan and its analogue, whereas as can be seen in the results of Examples 10 and 12, the gene derived from *Herbaspirillum rhizosphaerae* improved L-tryptophan production in both *Corynebacterium glutamicum* and E. coli strains. Additionally, it was observed in Example 11 that the gene derived from *Herbaspirillum rhizosphaerae* substantially exported tryptophan extracellularly. As a result, the gene derived from *Herbaspirillum rhizosphaerae* was named as wex (tryptophan (W) exporter).

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A microorganism producing L-tryptophan, wherein the microorganism expresses a protein having L-tryptophan-exporting activity and comprising the amino acid sequence of SEQ ID NO: 1, and
   wherein the microorganism is *Corynebacterium glutamicum*.

2. A microorganism producing L-tryptophan, wherein the microorganism expresses a protein having L-tryptophan-exporting activity and comprising the amino acid sequence of SEQ ID NO: 1, and wherein the microorganism is *Escherichia coli*.

3. A method for producing L-tryptophan, comprising:
   culturing a microorganism producing L-tryptophan in a medium, wherein the microorganism expresses a protein having L-tryptophan-exporting activity and comprising the amino acid sequence of SEQ ID NO: 1, and wherein the microorganism is *Corynebacterium glutamicum*; and
   recovering the L-tryptophan from the cultured microorganism or cultured medium.

4. A method for producing L-tryptophan, comprising:
   culturing a microorganism producing L-tryptophan in a medium, wherein the microorganism expresses a protein having L-tryptophan-exporting activity and comprising the amino acid sequence of SEQ ID NO: 1, wherein the microorganism is *Escherichia coli*, and
   recovering the L-tryptophan from the cultured microorganism or cultured medium.

* * * * *